(12) United States Patent
Koehler

(10) Patent No.: US 10,369,273 B2
(45) Date of Patent: Aug. 6, 2019

(54) INTERLOCKING BASE FOR MOBILE STAND FOR USE WITH INTRAVENOUS DELIVERY OF MEDICATIONS

(71) Applicant: Pedigo Products, Inc., Vancouver, WA (US)

(72) Inventor: Randal W. Koehler, Woodland, WA (US)

(73) Assignee: PEDIGO PRODUCTS, INC., Vancouver, WA (US)

( * ) Notice: Subject to any disclaimer, the term of this patent is extended or adjusted under 35 U.S.C. 154(b) by 0 days.

(21) Appl. No.: 15/628,570

(22) Filed: Jun. 20, 2017

(65) Prior Publication Data

US 2017/0361013 A1  Dec. 21, 2017

Related U.S. Application Data

(60) Provisional application No. 62/352,954, filed on Jun. 21, 2016.

(51) Int. Cl.
| | |
|---|---|
| *A61M 5/14* | (2006.01) |
| *F16M 11/04* | (2006.01) |
| *F16M 11/42* | (2006.01) |
| *F16M 13/00* | (2006.01) |

(Continued)

(52) U.S. Cl.
CPC ........ *A61M 5/1413* (2013.01); *A61M 5/1415* (2013.01); *A61M 5/1417* (2013.01);
(Continued)

(58) Field of Classification Search
CPC .............. A61M 5/1417; A61M 5/1413; A61M 2209/084; A61M 5/1415; F16M 2200/08

USPC .............................................. 248/129; 482/68
See application file for complete search history.

(56) References Cited

U.S. PATENT DOCUMENTS 1,493,189 A * 5/1924 Carmeroto .............. F24B 15/00
  211/107
3,276,786 A * 10/1966 Olander .................... B62B 1/12
  280/33.997

(Continued)

FOREIGN PATENT DOCUMENTS

CA  2896090 A1 *  6/2014  .......... A61M 5/1415
EP  3034107 A1 *  6/2016  ............. B62B 3/102

(Continued)

OTHER PUBLICATIONS

Notice of Allowance, dated Feb. 21, 2018, received in U.S. Appl. No. 29/599,222.

*Primary Examiner* — Eret C McNichols
(74) *Attorney, Agent, or Firm* — Davis Wright Tremaine LLP; Heather M. Colburn

(57) ABSTRACT

A base having legs supported on wheels. A second leg may be positioned between first and third legs and the first leg may be positioned between the second leg and a fourth leg. A first gap is positioned between the second and third legs, and a second gap is positioned between the fourth and first legs. The first and second gaps are configured to at least partially receive a user's first and second feet, respectively. A keyway with a bridge may be defined between the first and second legs. A key that may be formed in a fifth leg is removably receivable inside a like keyway of a like base to thereby interlock the bases together so that they are moveable as a unit. An end portion of the key is positionable underneath a like bridge of the like keyway such that the like bridge limits upward movement of the key.

26 Claims, 21 Drawing Sheets

US 10,369,273 B2
Page 2

(51) Int. Cl.
 *F16M 11/16* (2006.01)
 *A61G 12/00* (2006.01)
 *F16M 11/00* (2006.01)

(52) U.S. Cl.
 CPC ........... *F16M 11/04* (2013.01); *F16M 11/043* (2013.01); *F16M 11/42* (2013.01); *F16M 13/00* (2013.01); *A61G 12/008* (2013.01); *A61G 2203/00* (2013.01); *A61M 5/14* (2013.01); *A61M 5/1414* (2013.01); *A61M 2209/084* (2013.01); *F16M 11/00* (2013.01); *F16M 11/16* (2013.01); *F16M 2200/02* (2013.01); *F16M 2200/08* (2013.01)

(56) References Cited

U.S. PATENT DOCUMENTS

| | | | | |
|---|---|---|---|---|
| 3,552,577 | A * | 1/1971 | Latham, Jr. | A61B 10/0096 211/74 |
| 3,642,241 | A * | 2/1972 | Kaufman | A61M 5/1415 211/117 |
| 3,977,567 | A * | 8/1976 | Rudd | A61M 5/16845 128/DIG. 13 |
| 4,289,244 | A * | 9/1981 | Frankhouser | A61M 5/1415 211/117 |
| 4,332,378 | A * | 6/1982 | Pryor | A61M 5/1415 135/67 |
| 4,756,706 | A * | 7/1988 | Kerns | A61M 5/1413 128/DIG. 13 |
| D308,725 | S | 6/1990 | Kraus | |
| 4,945,592 | A * | 8/1990 | Sims | A61G 7/05 248/129 |
| D325,440 | S | 4/1992 | Landis et al. | |
| D331,108 | S | 11/1992 | Curbbun | |
| 5,337,986 | A * | 8/1994 | Vollink | A47G 7/045 211/107 |
| 5,479,953 | A * | 1/1996 | Pasulka | A61H 3/04 135/66 |
| 5,556,065 | A * | 9/1996 | Wadley | A61M 5/1415 248/129 |
| 5,588,166 | A * | 12/1996 | Burnett | A61G 7/05 248/214 |
| 5,704,577 | A * | 1/1998 | Gordon | A61H 3/04 135/66 |
| 5,820,086 | A * | 10/1998 | Hoftman | A61M 5/1415 248/125.2 |
| 5,927,349 | A * | 7/1999 | Martucci | G05D 11/131 141/104 |
| D419,674 | S | 1/2000 | Schattner | |
| D435,107 | S | 12/2000 | Blair et al. | |
| 6,367,749 | B2 | 4/2002 | Valiulis | |
| 6,390,311 | B1 * | 5/2002 | Belokin | A61M 5/1415 211/189 |
| 6,682,055 | B1 * | 1/2004 | Tomlinson | E01F 13/022 248/129 |
| D559,390 | S | 1/2008 | Diener et al. | |
| 7,343,224 | B2 * | 3/2008 | DiGianfilippo | A61K 9/0019 141/100 |
| 7,631,773 | B1 * | 12/2009 | Calabrisotto | A47B 61/00 211/196 |
| D627,063 | S | 11/2010 | West et al. | |
| D628,691 | S | 12/2010 | Sung et al. | |
| 7,849,537 | B2 * | 12/2010 | Graham | A61G 7/0503 248/222.11 |
| 7,896,298 | B2 * | 3/2011 | Meyers | A61M 5/1415 248/124.1 |
| 7,896,299 | B2 * | 3/2011 | Chinuki | F16M 11/10 248/127 |
| 7,935,030 | B1 * | 5/2011 | Nesbitt | A61H 3/04 482/142 |
| 7,976,508 | B2 * | 7/2011 | Hoag | A61M 5/1413 340/572.1 |
| 8,011,707 | B1 * | 9/2011 | Summers | A47C 1/124 280/47.35 |
| D657,470 | S | 4/2012 | Schon et al. | |
| 8,196,874 | B2 | 6/2012 | Zitting et al. | |
| 8,292,310 | B2 * | 10/2012 | Turner | A61H 3/04 280/47.34 |
| 8,313,066 | B2 * | 11/2012 | Hampton | A61M 5/1415 16/30 |
| 8,313,067 | B2 * | 11/2012 | Knieriem | F16M 11/42 248/129 |
| 8,403,275 | B2 * | 3/2013 | Cote | A61M 5/1415 211/85.18 |
| 8,555,904 | B1 | 10/2013 | Lai | |
| D703,329 | S * | 4/2014 | Worcester | D24/185 |
| 8,684,375 | B2 * | 4/2014 | Fink | B60B 33/0026 248/129 |
| D728,096 | S * | 4/2015 | Yamamoto | D24/128 |
| 9,370,617 | B2 * | 6/2016 | Chepurny | A61G 12/008 |
| D796,047 | S | 8/2017 | Janzen | |
| 9,737,654 | B2 * | 8/2017 | Walther | A61M 5/1415 |
| 9,814,828 | B2 * | 11/2017 | Thompson | A61M 5/1414 |
| D820,978 | S | 6/2018 | Koehler | |
| 2002/0035412 | A1 * | 3/2002 | Kircher | B01F 13/1063 700/239 |
| 2002/0047075 | A1 * | 4/2002 | Metz | A61G 7/0503 248/229.1 |
| 2005/0116126 | A1 * | 6/2005 | Ugent | A61M 5/1415 248/129 |
| 2005/0139736 | A1 * | 6/2005 | Breda | A61M 5/1415 248/129 |
| 2006/0278771 | A1 * | 12/2006 | Ho | A61G 7/1017 248/122.1 |
| 2007/0063460 | A1 * | 3/2007 | O'Quin | B62B 3/1404 280/33.992 |
| 2008/0035804 | A1 * | 2/2008 | Ferguson | A61M 5/1415 248/157 |
| 2008/0054132 | A1 * | 3/2008 | Muncie | A61M 5/1415 248/176.1 |
| 2009/0058033 | A1 * | 3/2009 | Tomlinson | A61H 3/04 280/200 |
| 2009/0146027 | A1 * | 6/2009 | Zitting | A61M 5/1415 248/176.1 |
| 2009/0294604 | A1 * | 12/2009 | Sunderland | A61M 5/1415 248/124.1 |
| 2010/0052274 | A1 * | 3/2010 | West | A61M 5/1417 280/47.24 |
| 2010/0187785 | A1 * | 7/2010 | Knappe | A61G 12/001 280/47.34 |
| 2012/0119045 | A1 * | 5/2012 | Gaal | A61M 5/1415 248/219.4 |
| 2013/0168526 | A1 | 7/2013 | Walther et al. | |
| 2013/0181100 | A1 * | 7/2013 | Blankenship | A61M 5/1415 248/129 |
| 2013/0228997 | A1 * | 9/2013 | Fukuhara | A61G 5/10 280/304.1 |
| 2014/0209550 | A1 * | 7/2014 | Pryor | A61M 5/1417 211/85.13 |
| 2014/0259837 | A1 * | 9/2014 | Belliveau | A61M 5/1415 40/673 |
| 2014/0278156 | A1 * | 9/2014 | Thompson | A61M 5/16831 702/55 |
| 2016/0022900 | A1 * | 1/2016 | Pryor | A61M 5/1415 248/218.4 |
| 2016/0114102 | A1 * | 4/2016 | Yamamoto | A61M 5/1415 108/27 |
| 2016/0270530 | A1 * | 9/2016 | Heyring | A47B 1/16 |
| 2016/0273701 | A1 * | 9/2016 | Heyring | A47B 13/023 |
| 2017/0340813 | A1 * | 11/2017 | Walther | F16M 13/02 |

FOREIGN PATENT DOCUMENTS

| | | | | |
|---|---|---|---|---|
| JP | 2013135882 | A * | 7/2013 | ......... A61M 5/1415 |
| JP | 2014061437 | A * | 4/2014 | ......... A61M 5/1415 |
| WO | WO-2014194388 | A1 * | 12/2014 | ......... A61M 5/1415 |
| WO | 2016077729 | | 5/2016 | |

* cited by examiner

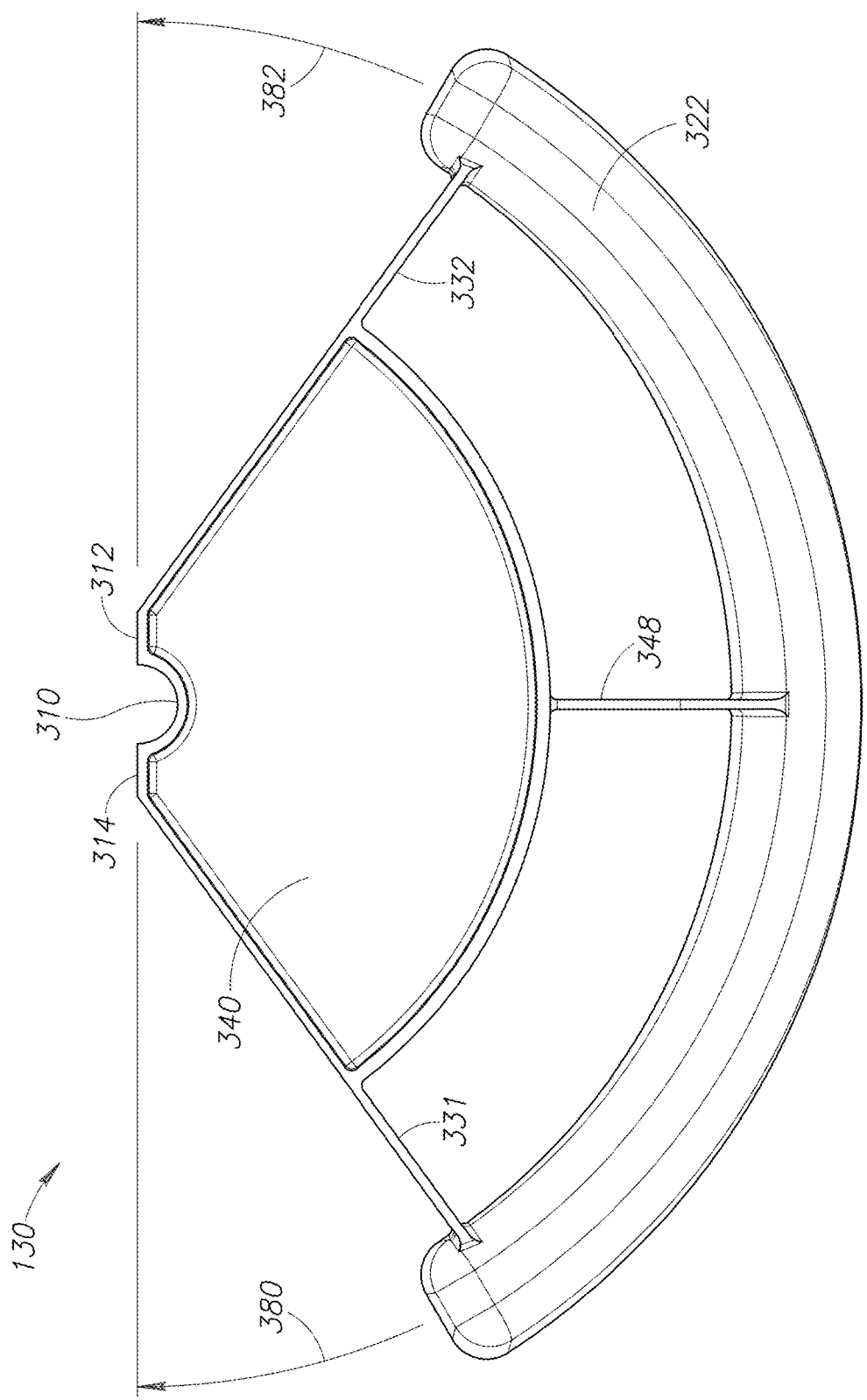

INTERLOCKING BASE FOR MOBILE STAND FOR USE WITH INTRAVENOUS DELIVERY OF MEDICATIONS

CROSS REFERENCE TO RELATED APPLICATION

This application claims the benefit of U.S. Provisional Application No. 62/352,954, filed on Jun. 21, 2016, which is incorporated herein by reference in its entirety.

BACKGROUND

Field of the Invention

The present invention is directed generally to poles or stands for intravenous drugs (commonly referred to as IV stands).

Description of the Related Art

A conventional IV stand has three components: a wheeled base, a push handle, and a hook assembly or attachment. Unfortunately, prior art IV stands suffer from many shortcomings.

For example, in a hospital, it is desirable for one person (e.g., a caregiver) to safely maneuver several (more than one in each hand) IV stands at once (e.g., down a hallway) to various locations. It is also desirable for one person (e.g., a janitor) to bring several IV stands to the same location at the same time (e.g., at the end of a day shift for cleaning and sanitizing). Unfortunately, prior art IV stands allow one person to safely move a maximum of two IV poles (one in each hand). This means multiple trips must be made, which take more time and, therefore, add expense.

At least one prior art IV stand (e.g., a SmartStack IV Stand manufactured by Maxtec or ALCO) includes a "towable" type base that requires a separate adapter to lock two of the IV stands together so that they may be towed or pushed together in a "controlled manner." Multiple adaptors must be used to couple multiple IV stands together. Unfortunately, in hospitals, these adaptors are often lost and are therefore not used. When this occurs, controlled towing of the IV stands is not possible.

Further, patients connected to one or more of the bags mounted on an IV stand sometimes must walk and push the IV stand. Unfortunately, many prior art IV stands have symmetrical "star" shaped bases. Such star shaped bases include legs that extend outwardly radially from a center of the base. Depending on orientation of the IV stand, these legs can get in the way (e.g., of a patient walking next to the IV stand) and may create a trip hazard.

Additionally, conventional IV stands typically have a push handle that is not ergonomically designed. To use such handles, the user must twist his/her wrist, which may cause undo strain to the user's hand and/or wrist resulting in discomfort.

Conventional IV stands also position multiple IV bags such that some of the bags obscure labels on others of the bags. To read the labels, a caregiver must reposition the bags, which can be difficult if the bags are attached to a patient (e.g., by medication lines). Therefore, conventional IV stands may contribute to label reading errors and misidentification of the IV bags, which may pose a risk to the patient.

Therefore, a need exists for new IV stands. In particular, a need exists for an IV stand that does not require an adapter to interconnect two or more IV stands. An IV stand with a base that avoids interfering with the feet of a patient as the patient pushes the IV stand would be particularly desirable. A need also exists for a more ergonomically designed push handle. Additionally, a need exists for a hook attachment for an IV stand that makes it easier to read the labels on the IV bags. The present application provides these and other advantages as will be apparent from the following detailed description and accompanying figures.

BRIEF DESCRIPTION OF THE SEVERAL VIEWS OF THE DRAWINGS

FIG. 10 is a top view of the push handle of FIG. 6.

Like reference numerals have been used in the figures to identify like components.

DETAILED DESCRIPTION

Figure 1:
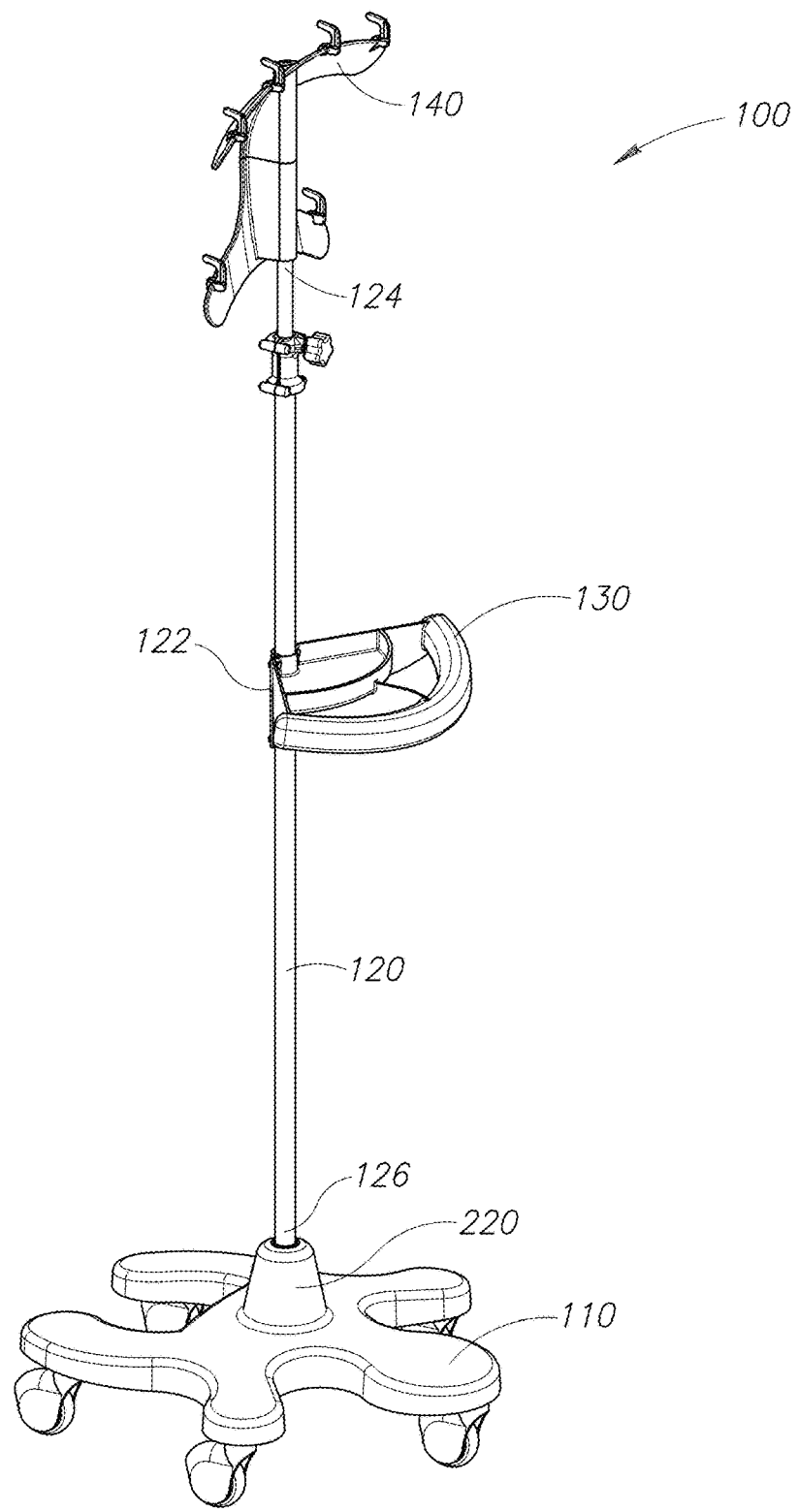
FIG. 1 is a perspective view of an IV stand.
Figure 13A:
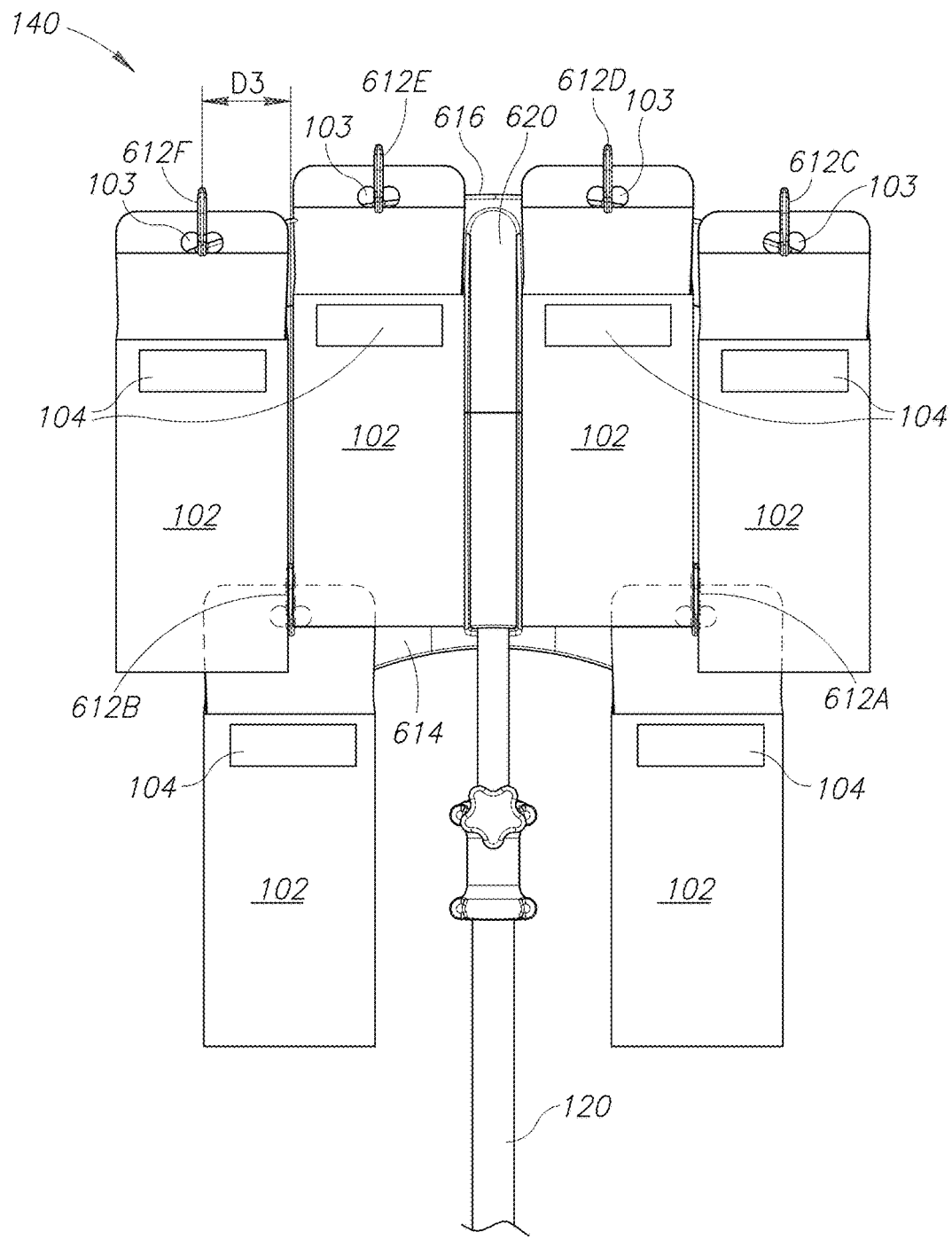
FIG. 13A is a rear view of the hook attachment of FIG. 12 illustrated with IV bags hanging therefrom.
Figure 13B:
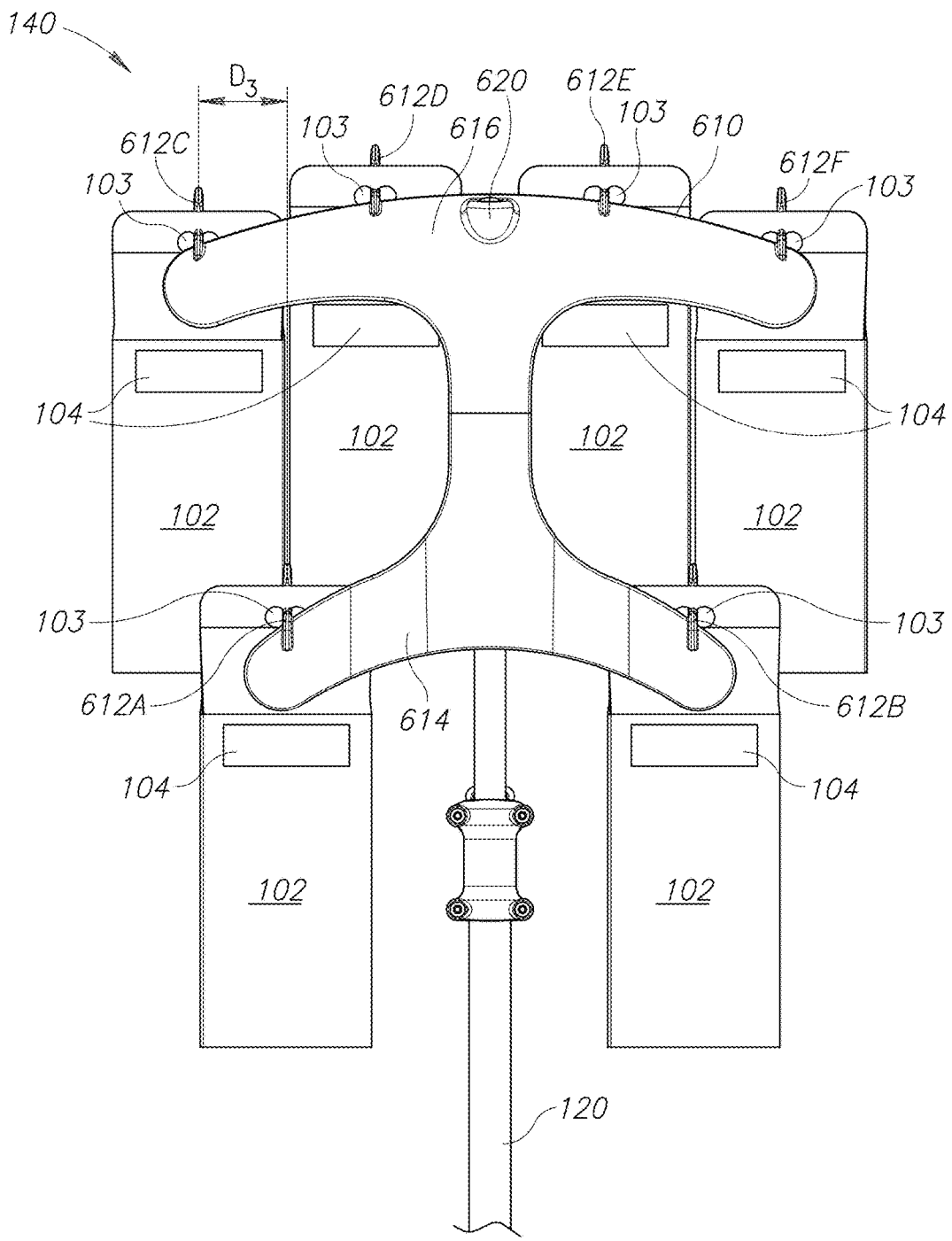
FIG. 13B is a front view of the hook attachment of FIG. 12 illustrated with IV bags hanging therefrom.

FIG. 1 is a perspective view of a stand or pole, referred to hereafter as an "IV stand" 100. One or more bags 102 (see FIGS. 11A, 11B, 13A-14B, 17, and 18) may be mounted on the IV stand 100. Referring to FIGS. 13A and 13B, the bags 102 store solutions (e.g., saline, drugs, blood, etc.) delivered intravenously (via medication lines 106 illustrated in FIGS. 11A and 11B) to one or more patients (not shown). Referring to FIG. 1, the IV stand 100 includes an interlocking base 110, a pole 120, a mounting bracket 122, an ergonomic push handle 130, and a hook attachment 140. Referring to FIGS.

13A and 13B, each of the bags 102 has an opening 103 configured to be attached to (or hooked on) the hook attachment 140. Each of the bags 102 also has indicia (referred to as a label 104) that identifies the contents of the bag.

Interlocking Base

Figure 2:
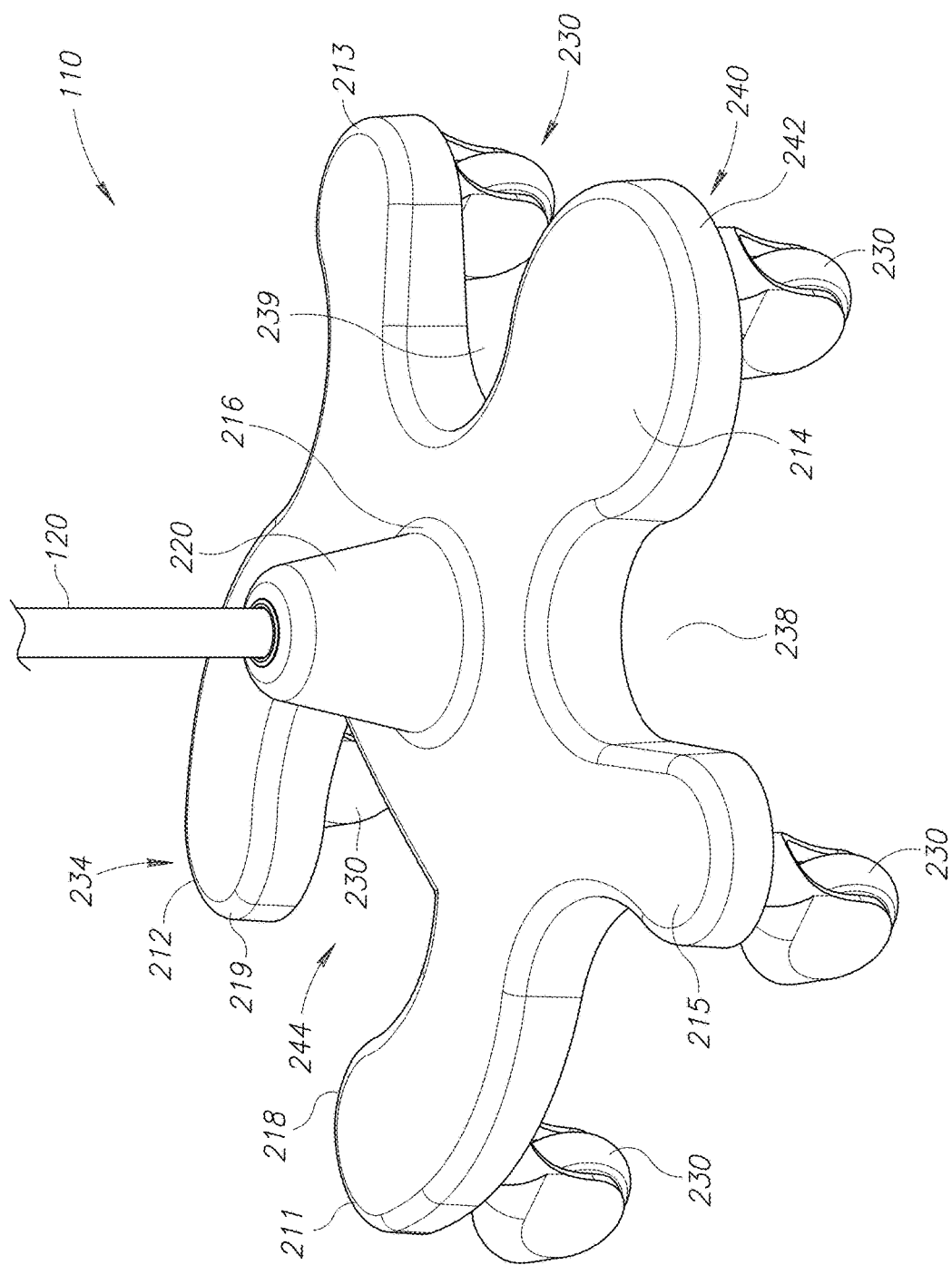
FIG. 2 is a perspective view of a base of the IV stand of FIG. 1.

Referring to FIG. 1, the base 110 is configured to be mounted to the pole 120 of the IV stand 100, a pole on a conventional IV stand, a pole of similar mobile equipment, and the like. The base 110 is configured to support and provide stability to the IV stand 100 and to provide a location to mount wheels 230 (see FIGS. 2, 4, and 5), casters (not shown), and the like. FIG. 2 is an enlarged perspective view of the base 110. As will be explained below, the base 110 is configured to interlock with a base of another IV stand like the IV stand 100 (see FIG. 1). When the bases are interlocked together, the IV stands may be push or pulled together as a unit. Additionally, as will also be explained below, the base 110 is configured to allow a user (e.g., a patient) to walk more closely to the base 110 than would be possible with a conventional IV stand without posing a trip hazard to the user.

As shown in FIG. 2, the base 110 has a plurality of support legs 211-215 that extend outwardly from a center section 216. The center section 216 has a connector 220 configured to receive and retain the pole 120. Each of the legs 211-215 rests upon and is supported by a caster or the wheel 230. Thus, the legs 211-215 provide mounting locations for the wheels 230. When the base 110 is pushed or pulled, the base 110 rolls on the wheels 230.

Figure 4:
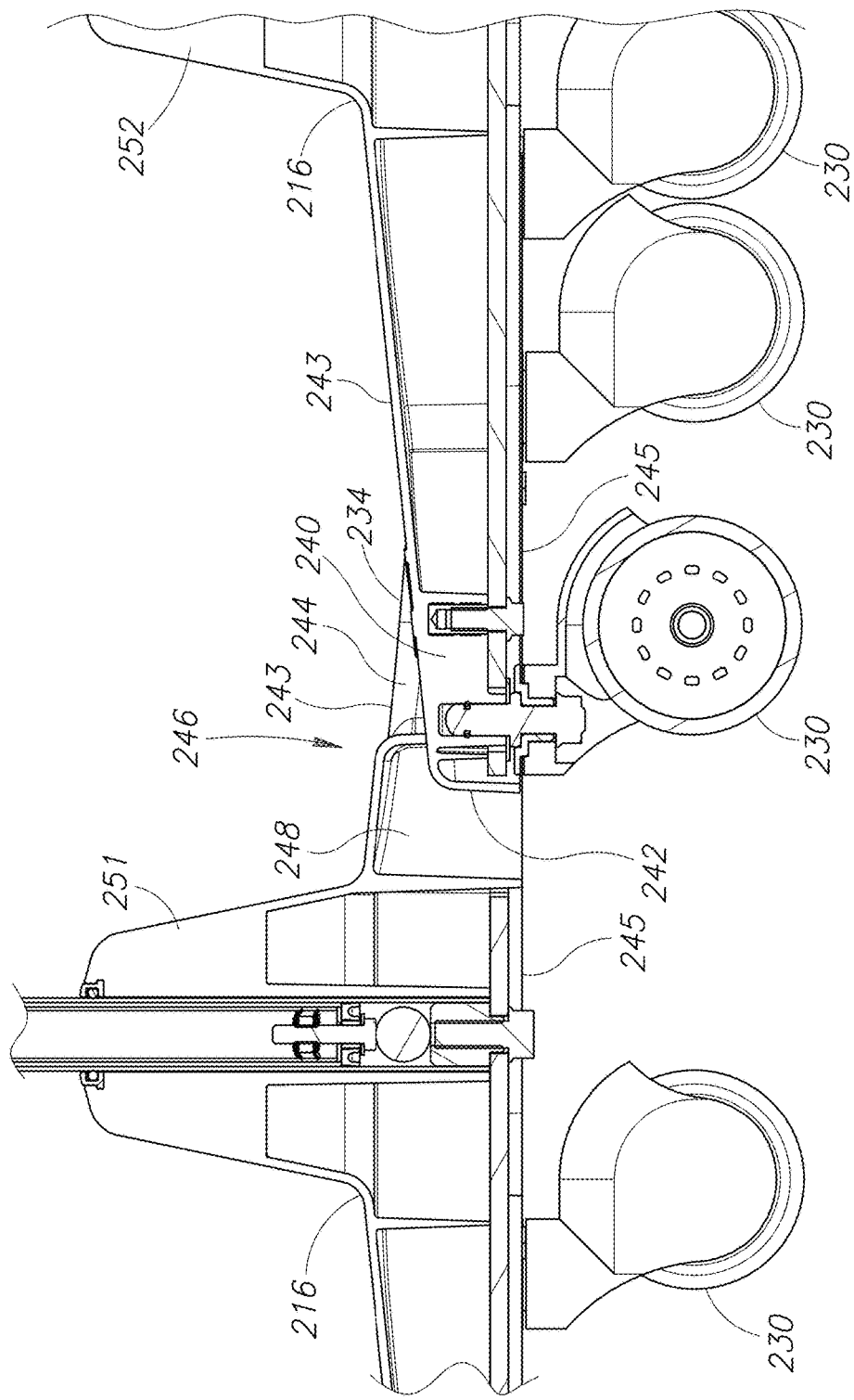
FIG. 4 is an enlarged cross-sectional view of portions of two of the interlocked bases of FIG. 3 taken through a plane defined by x and z-axes shown in FIG. 3.

The legs 211-215 may each taper outwardly and downwardly from the center section 216 along their upper surfaces 243 (see FIG. 4), which are opposite bottom surfaces 245 (see FIG. 4). Referring to FIG. 4, in the embodiment illustrated, the upper surfaces 243 may be characterized as being formed along a cone having an apex at or near the center section 216.

Referring to FIG. 2, the legs 211 and 212 may be characterized as defining a socket shaped tail section 234. The tail section 234 has a keyway 244 formed therein between the legs 211 and 212. Opposite the center section 216, the legs 211 and 212 have curved end portions 218 and 219, respectively. The curved end portions 218 and 219 curve toward the keyway 244. Referring to FIG. 4, a bridge section 246 overhangs a portion 248 of the keyway 244.

Referring to FIG. 2, a gap 238 is defined between the legs 214 and 215. A gap 239 is defined between the legs 213 and 214. The gap 238 is configured to receive the end portion 218 of the leg 211 and the gap 239 is configured to receive the end portion 219 of the leg 212.

The leg 214 has a sloped radial shaped head section 240. The head section 240 tapers toward its distal edge portion 242. The head section 240 may be characterized as being a key configured to be removable received inside the keyway 244. Thus, the head section 240 may be mated with the tail section 234. The keyway 244 may be characterized as having a radial socket shape and the head section 240 may be characterized as having a matching or corresponding radial shape. The curved end portions 218 and 219 of the legs 211 and 212, respectively, curve around the head section 240 and help maintain or trap the head section 240 inside the keyway 244. Thus, the keyway 244 is configured to receive and retain the head section 240 therein.

Figure 3:
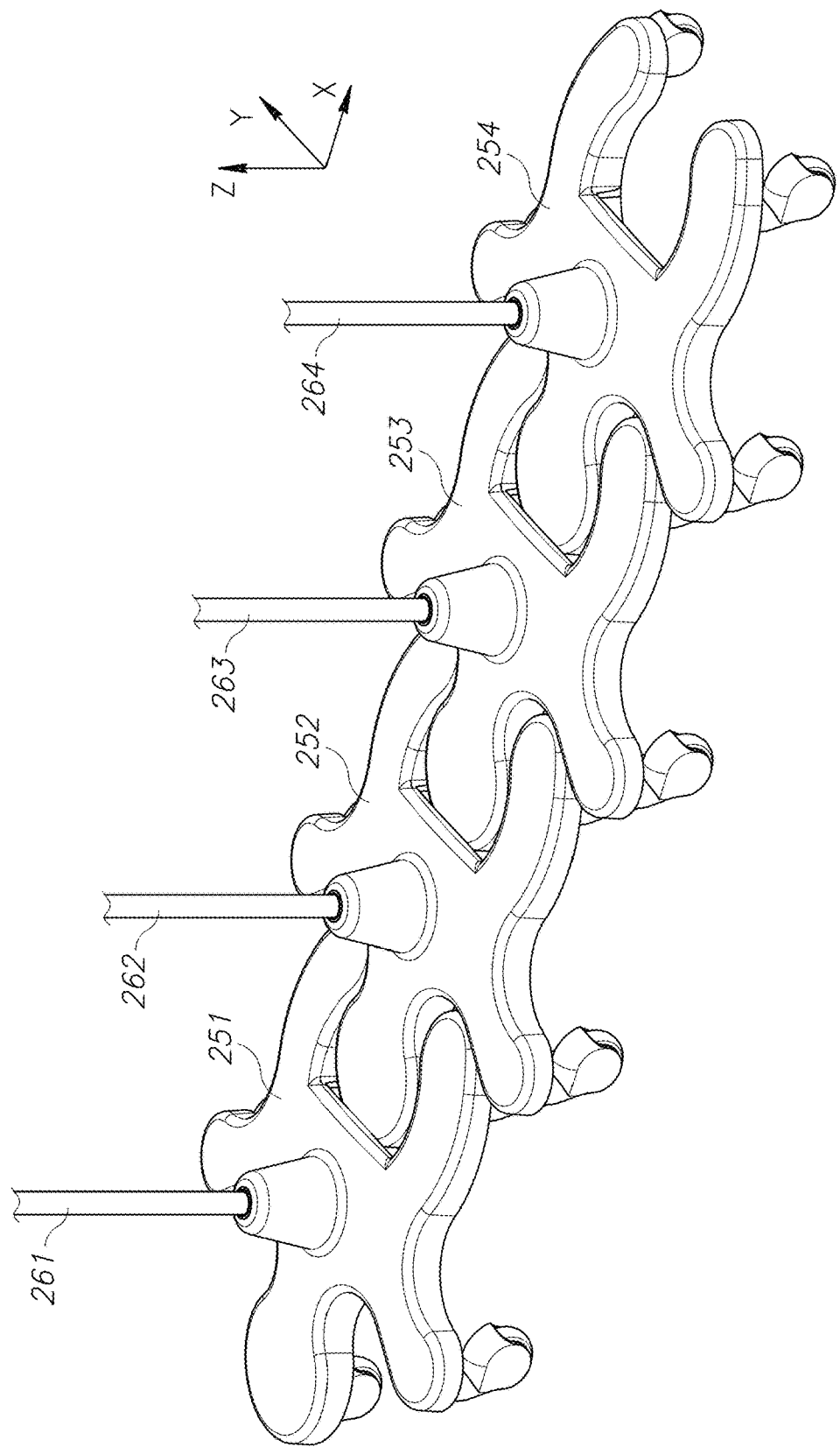
FIG. 3 is a perspective view of four bases, each like the base of FIG. 2, interlocked together.

Referring to FIG. 3, a series of multiple bases 251-254 (each like the base 110 illustrated in FIGS. 1, 2, and 5) of multiple IV stands 261-264 (each like a conventional IV stand or the IV stand 100 illustrated in FIG. 1) may be interlocked together so that the bases 251-254 may be pushed together as a unit. Referring to FIG. 4, for ease of illustration, the interlocking of the forward base 251 and the aft base 252 will be described in greater detail. However, as shown in FIG. 3, more than two of the bases 251-254 may be interlocked together. For example, the forward base 251 may be interlocked with the aft base 252, the forward base 251 may be interlocked with the aft base 253, and the forward base 253 may be interlocked with the aft base 254. Any number of forward and aft bases may be interlocked in this manner. When interlocked, the bases 251-254 may be pushed or pulled (e.g., down a hallway) at the same time and in a controlled manner without the use of a separate link or adaptor. The bases 251-254 simply interlock together in a series.

Referring to FIG. 4, the forward and aft bases 251 and 252 are interlocked together by placing the head section 240 of the aft base 252 near the tail section 234 of the forward base 251. Then, the tail section 234 of the forward base 251 is raised (e.g., by tipping the forward base 251 toward its head section 240). Next, the keyway 244 of the forward base 251 is lowered to position the head section 240 of the aft base 252 inside the keyway 244, which engages (or interlocks) the head section 240 with the keyway 244 thereby interlocking the forward and aft bases 251 and 252 together. Thus, the head section 240 of the aft base 252 may be locked into the tail section 234 of the forward base 251 to lock the bases 251 and 252 together. This process may be repeated for any number of pair of forward and aft bases (e.g., the series of bases 251-254 illustrated in FIG. 3).

When the head section 240 of the aft base 252 is inside the keyway 244 of the forward base 251, the distal edge portion 242 of the head section 240 of the aft base 252 is positioned under the bridge section 246 of the forward base 251. Thus, the bridge section 246 of the forward base 251 is positioned over the distal edge portion 242 of the head section 240 of the aft base 252 and limits upward movement of the head section 240 relative to the forward base 251 (e.g., when the bases 251 and 252 are moved together along the floor and/or over an obstacle). The head section 240 of the aft base 252 may maintain or support the forward base 251 vertically. For example, the bridge section 246 of the forward base 251 may contact (or rest on) the head section 240 of the aft base 252. Alternatively, a pre-determined gap (not shown) may be defined between the upper surface 243 of the head section 240 and the bridge section 246. In other words, the bridge section 246 may straddle the head section 240 and be spaced apart therefrom by the pre-determined gap (not shown). Additionally, a gap (not shown) may be defined along the head section 240 of the aft base 252 between the head section 240 of the aft base 252 and the keyway 244 of the forward base 251.

The tail section 234 of the forward base 251 may articulate (or move) with respect to the head section 240 of the aft base 252 when the bases 251 and 252 are interlocked together. For example, the tail section 234 of the forward base 251 may articulate (or rotate) about a y-axis (see FIG. 3) by a limited amount to traverse the terrain and obstacles (e.g., bumps, thresholds, changes in elevation, changes in slope of the terrain, and the like) with respect to the head section 240 of the aft base 252 before the head section 240 of the aft base 252 disengages from the keyway 244 of the forward base 251. Referring to FIG. 3, the forward and aft bases 251 and 252 may be rotated about a z-axis by a limited amount, which is determined (or controlled) by dimensional clearance between the tail and head sections 234 and 240 (see FIGS. 2 and 4) of the forward and aft bases 251 and 252, respectively. Further, depending upon the implementation details, the forward and aft bases 251 and 252 may move with respect to one another along x-axis.

Figure 5:
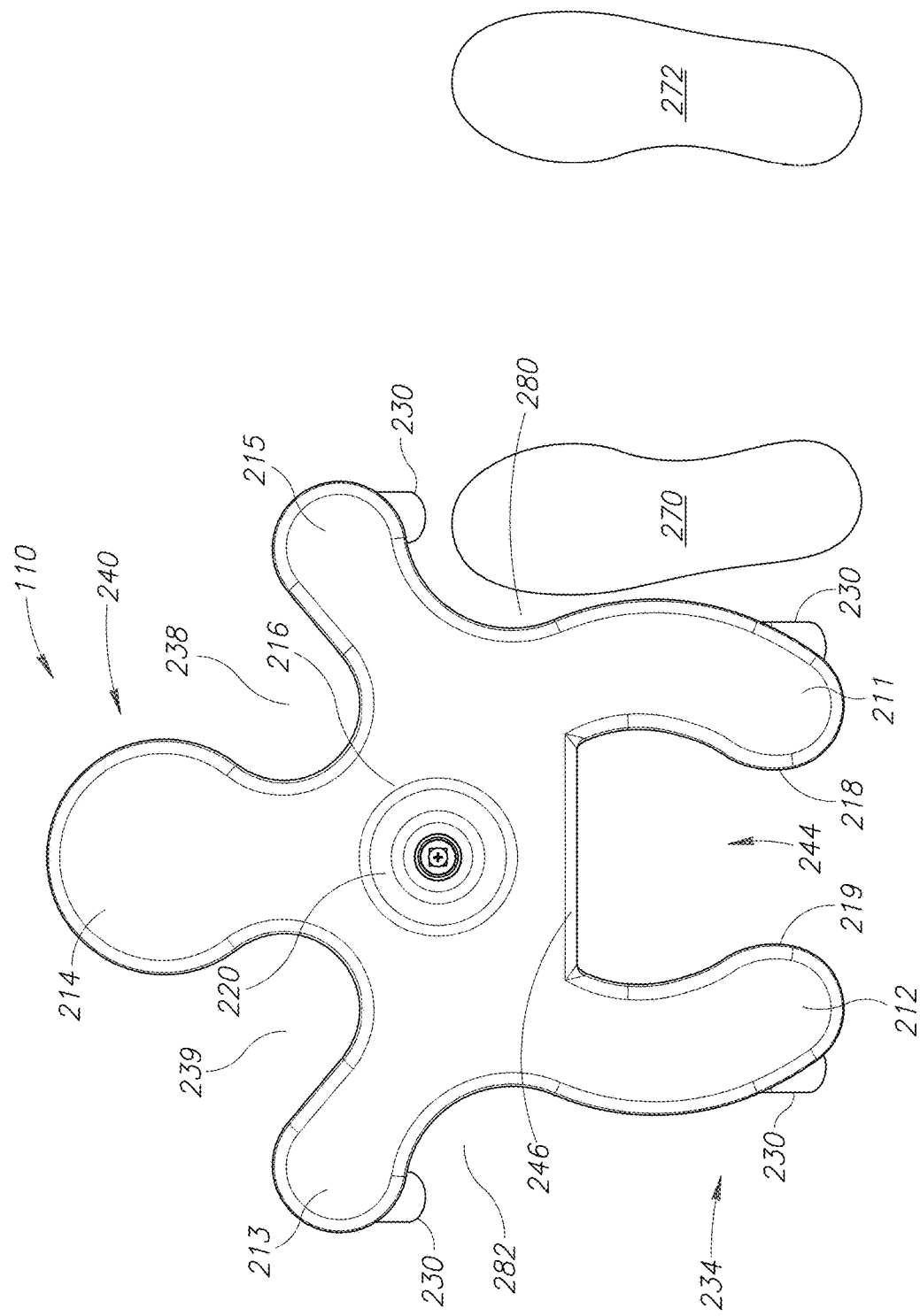
FIG. 5 is a top view of the base of FIG. 2 illustrated alongside a user's feet.

As shown in FIG. 5, the legs 211-213 and 215 do not extend radially from the center section 216. Thus, the outer shape of the base 110 allows a user's feet 270 and 272 to be placed closer to the IV stand 100 (see FIG. 1) than a prior art IV stand, thereby providing a more ergonomic and comfortable (natural) posture to allow better grip and control of the IV stand 100 (see FIG. 1) during movement. A first "clearance" gap 280 is defined between the legs 211 and 215, and a second "clearance" gap 282 is defined between the legs 212 and 213. Each of the clearance gaps 280 and 282 is configured to at least partially receive a user's foot or feet 270 and 272 when the user is standing or walking next to the base 110 thereby avoiding interference with the legs 211-215 of the base 110 and thus reducing a trip hazard.

By way of a non-limiting example, the base 110 may be constructed as a single piece. The base 110 may be constructed from an injection-molded polymer. However, alternate manufacturing methods may be employed to create the base 110, such as aluminum die-casting, sand casting, investment casting, machining, and the like.

Pole

Referring to FIG. 1, the pole 120 may be implemented as a conventional pole used to construct prior art IV stands. In the embodiment illustrated, the pole 120 has a generally cylindrical outer shape with a circular cross-sectional shape. However, this is not a requirement. The pole 120 extends from the base 110 to the hook attachment 140. The pole 120 is attached by its first end portion 124 to the hook attachment 140 and by its second end portion 126 to the connector 220 of the base 110. The mounting bracket 122 may couple the handle 130 to the pole 120 at a predetermined vertical location between the first and second end portions 124 and 126 of the pole 120. By way of a non-limiting example, the mounting bracket 122 may couple the handle 130 to the pole 120 at about 35 inches to about 45 inches from the floor.

Mounting Bracket

Figure 6:
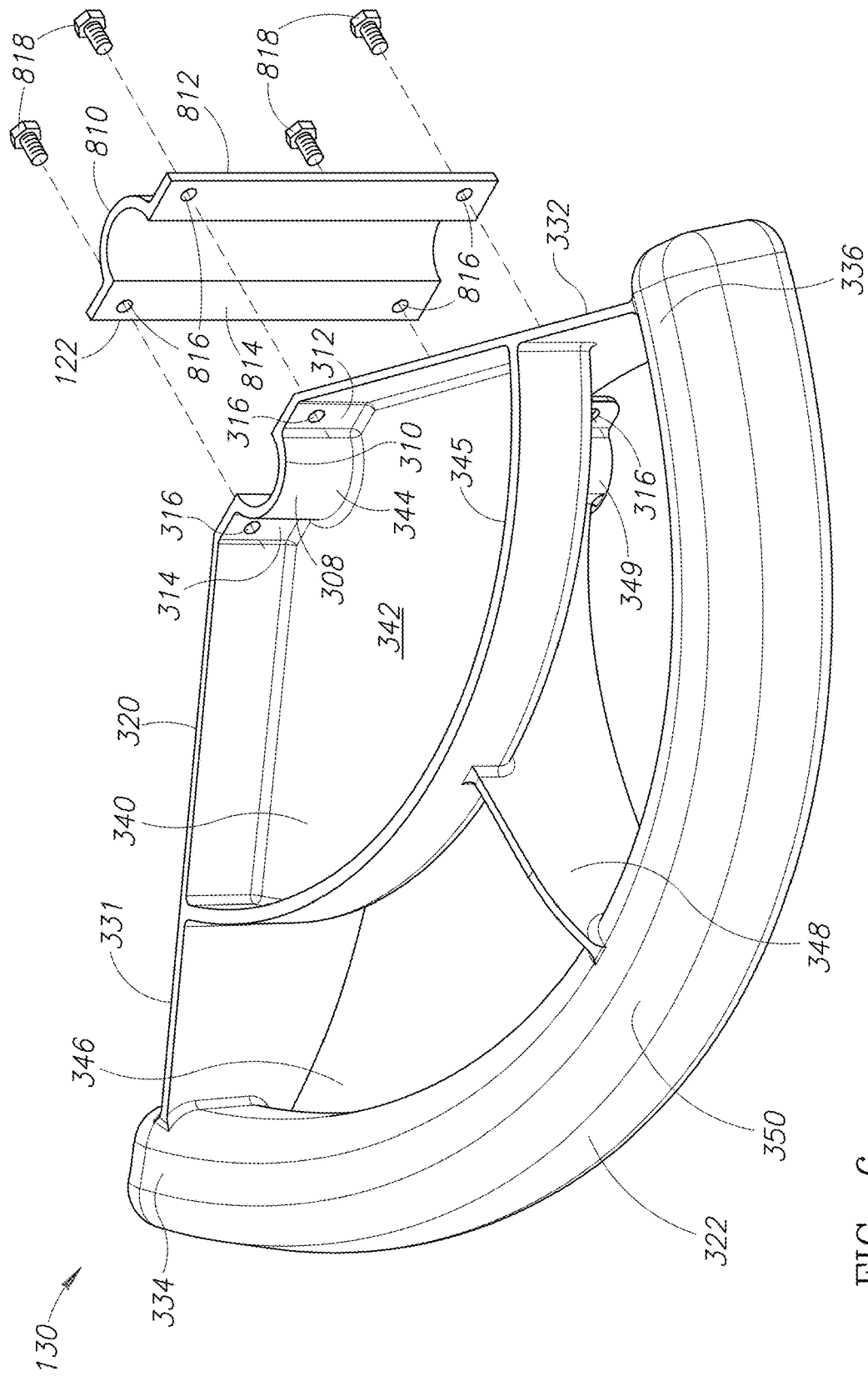
FIG. 6 is an exploded perspective view of a push handle and mounting bracket of the IV stand of FIG. 1.

FIG. 1 depicts the mounting bracket 122 coupling the handle 130 to the pole 120. Referring to FIG. 6, the mounting bracket 122 has a curved portion 810 flanked by planar sections 812 and 814. Each of the planar sections 812 and 814 includes one or more through-holes 816 each configured to receive a different fastener 818. The curved portion 810 is contoured to be positioned against the pole 120 (see FIGS. 1, 2, 12-14B, 17, and 18). The fasteners 818 are configured to be inserted one each into the through-holes 816. The fasteners 818 extend through the planar sections 812 and 814 and into the handle 130 with the pole 120 (see FIGS. 1, 2, 12-14B, 17, and 18) positioned alongside the curved portion 810 between the mounting bracket 122 and the handle 130. In this manner, the pole 120 may be clamped between the mounting bracket 122 and the handle 130.

Referring to FIG. 1, the mounting bracket 122 and the handle 130 may be clamped to the pole 120 (or another object having a generally circular cross-sectional shape) at any circumferential location along the pole 120. Thus, the mounting bracket 122 and the handle 130 do not have to be slid onto the pole 120 axially or from an axial position.

Handle

Referring to FIG. 1, the ergonomic push handle 130 is configured to be mounted on the pole 120 of the IV stand 100, a pole on a conventional IV stand, a pole of similar mobile equipment, and the like. In the embodiment illustrated, the handle 130 may be characterized as being a circular sector or generally pie-shaped. Thus, the handle 130 may extend about 90° around the pole 120. However, in alternate embodiments, the handle 130 or a portion thereof may extend further (e.g., about 180°) around the pole 120 or less far around the pole 120 (e.g., about 45°).

Referring to FIG. 6, the handle 130 has a connector portion 308 that is substantially similar to the mounting bracket 122. Thus, the connector portion 308 may include a curved portion 310 flanked by planar sections 312 and 314. Each of the planar sections 312 and 314 includes one or more through-holes 316 each configured to receive a different one of the fasteners 818. The curved portion 310 is contoured to be positioned against the pole 120 (see FIGS. 1, 2, 12-14B, 17, and 18). The fasteners 818 are configured to be inserted one each into the through-holes 816 (and extend through the planar sections 812 and 814) and into the through-holes 316 when the pole 120 (see FIGS. 1, 2, 12-14B, 17, and 18) is received in between (and clamped onto by) the curved portions 310 and 810. The fasteners 818 fasten the planar sections 312 and 314 to the planar sections 812 and 814, respectively, and apply a clamping pressure to the curved portion 810. Referring to FIG. 1, in this manner, the pole 120 is clamped between the mounting bracket 122 and the handle 130. Thus, the mounting bracket 122 couples the handle 130 to the pole 120.

In the embodiment illustrated, the handle 130 has a handle body 320 integrally formed (e.g., molded) with the connector portion 308. The handle body 320 has a curved handle grip 322 attached to first and second spokes 331 and 332. The first and second spokes 331 and 332 extend from the connector portion 308 to the handle grip 322. In the embodiment illustrated, the first spoke 331 is connected to a first end portion 334 of the handle grip 322 and the second spoke 332 is connected to a second end portion 336 of the handle grip 322.

An optional tray 340 may be included between the first and second spokes 331 and 332. In the embodiment illustrated, the first and second spokes 331 and 332 form angled sidewalls of the tray 340. In the embodiment illustrated, an upper portion 344 of the connector portion 308 functions as a rear sidewall of the tray 340. The tray 340 has a front sidewall 345 opposite the upper portion 344 of the connector portion 308. The upper portion 344 and the front sidewall 345 both extend between the first and second spokes 331 and 332. Thus, the first and second spokes 331 and 332, the upper portion 344, and the front sidewall 345 form sidewalls that enclose the tray 340. The tray 340 has a substantially planar bottom 342 that extends between the first and second spokes 331 and 332, the upper portion 344, and the front sidewall 345.

The tray 340 extends from the connector portion 308 part way toward the handle grip 322. A gap 346 is defined between the front sidewall 345 of the tray 340 and the handle grip 322. The gap 346 is configured to receive the user's fingers when the user grips the handle grip 322. In the embodiment illustrated, a support spoke 348 extends from the front sidewall 345 of the tray 340 to a central portion 350 of the handle grip 322. Also, in the embodiment illustrated, the support spoke 348 extends from the central portion 350 of the handle grip 322 under the bottom 342 of tray 340 and is attached to a bottom portion 349 of the connector portion 308. Thus, the support spoke 348 may bifurcate the gap 346 at or near the central portion 350 of the handle grip 322.

Figure 8:
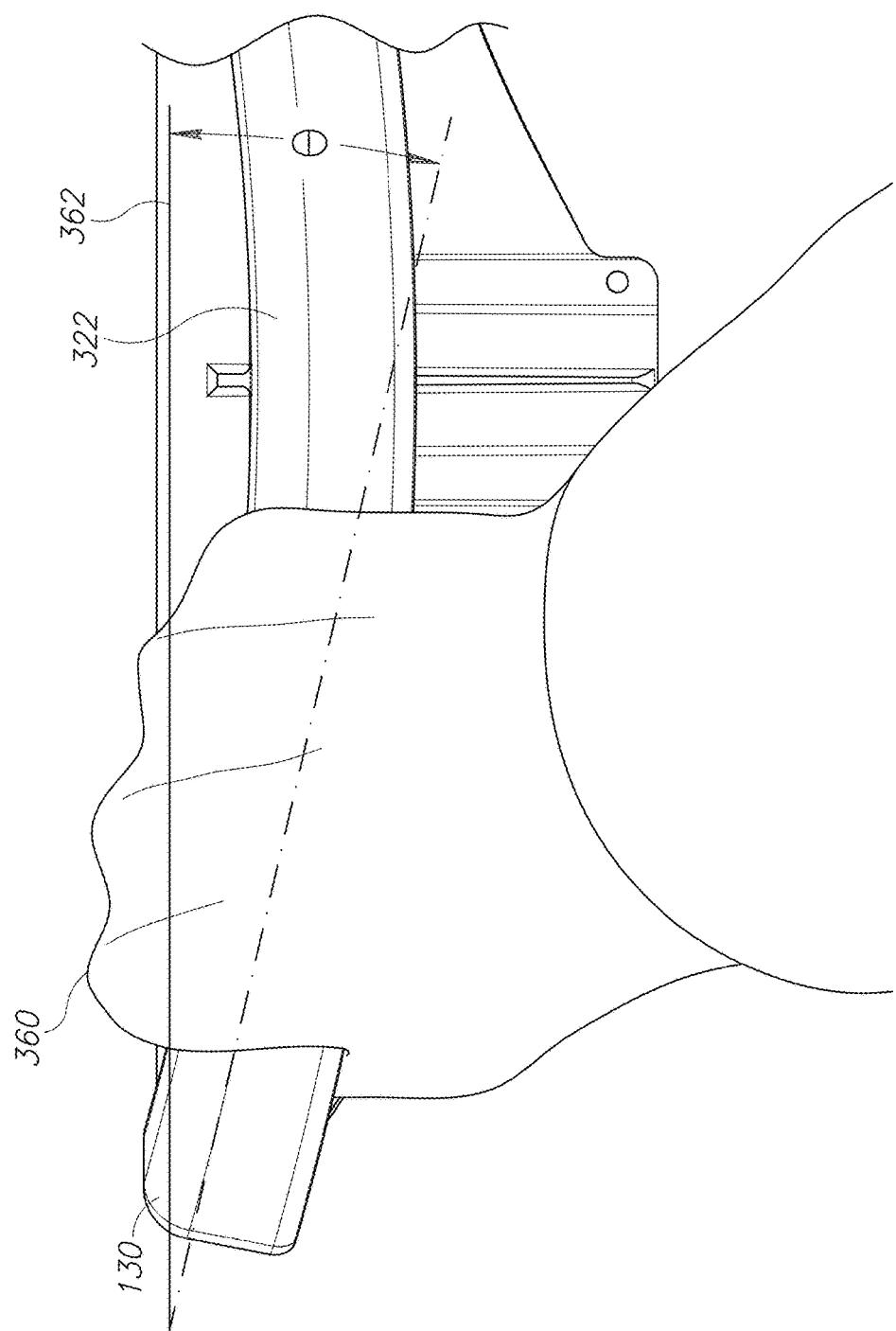
FIG. 8 is a perspective view of a right hand of a user gripping the push handle of FIG. 6.
Figure 9:
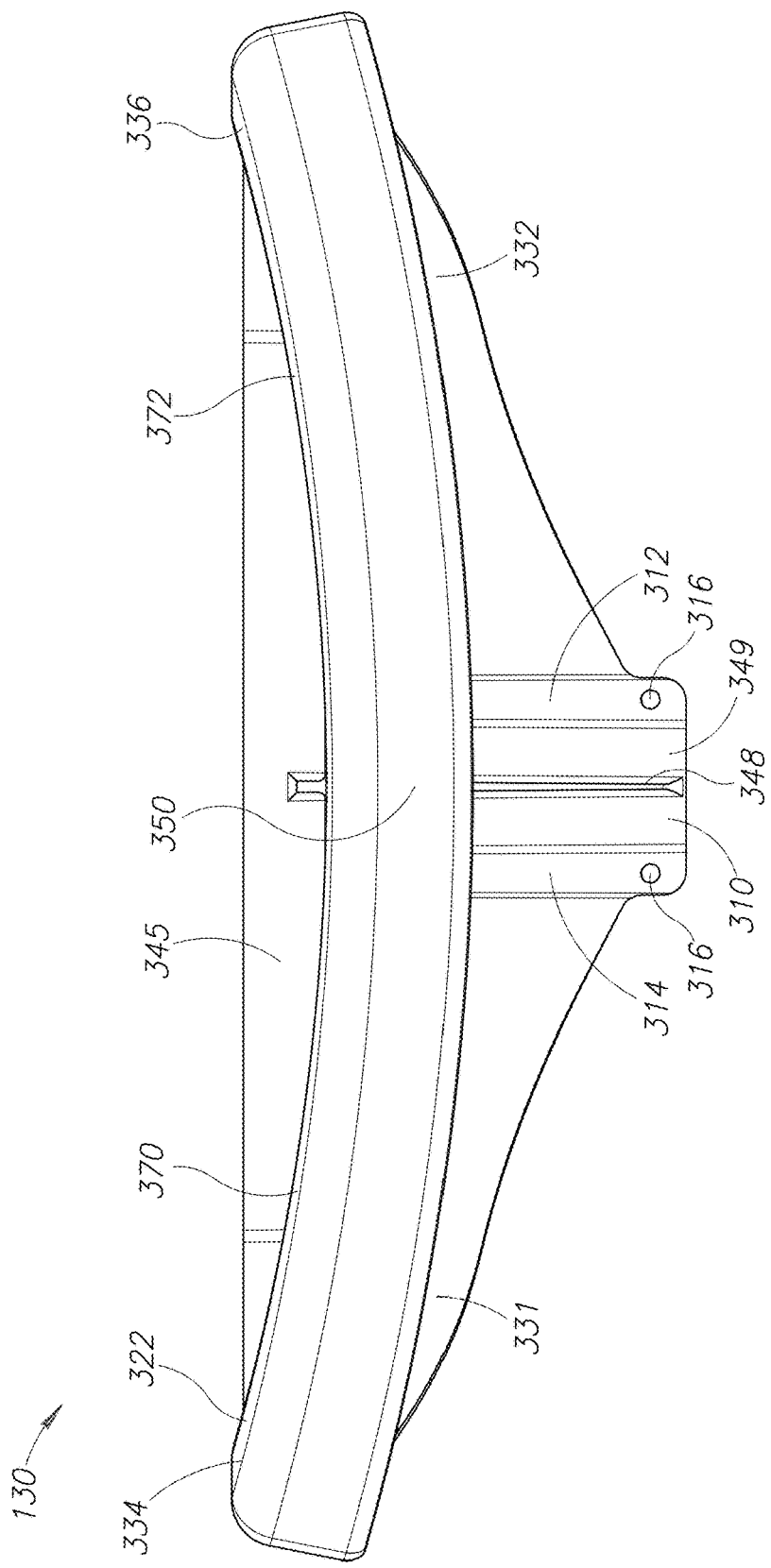
FIG. 9 is a front perspective view of the push handle of FIG. 6.

The central portion 350 is lower (i.e., closer to the floor) than the first and second end portions 334 and 336. Referring to FIG. 9, the first and second end portions 334 and 336 are connected to the central portion 350 by contoured or angled portions 370 and 372, respectively. Referring to FIG. 8, research has determined that the natural grip angle for a human hand (e.g., a right hand 360) is approximately 10 angular degrees from horizontal 362. The angled portions 370 and 372 (see FIG. 9) may each be angled at a predetermined angle θ with respect to horizontal 362. For example, the predetermined angle θ may be within a range of about 5° to about 15°. In some embodiments, the predetermined angle θ is 10°. Thus, the handle grip 322 may be characterized as having a "curved" grip profile or "curved" grip surface geometry. In some embodiments, the handle grip 322 may be generally U-shaped or V-shaped. In the embodiment illustrated, the angled portion 370 (see FIG. 9) is positioned to be gripped by the right hand 360 and the angled portion 372 (see FIG. 9) is positioned to be gripped by a left hand (not shown). Thus, the handle grip 322 provides a comfortable grip angle for both right-handed and left-handed users.

Figure 7A:
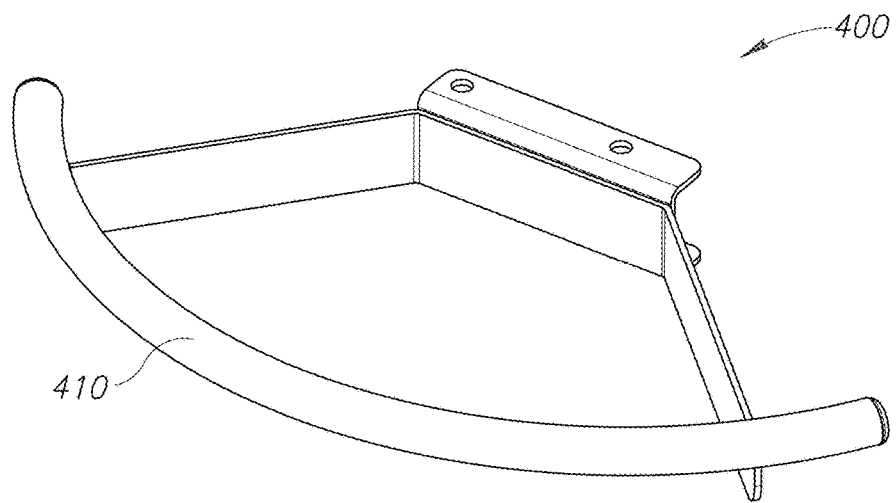
FIG. 7A is a perspective view of a prior art push handle.
Figure 7B:
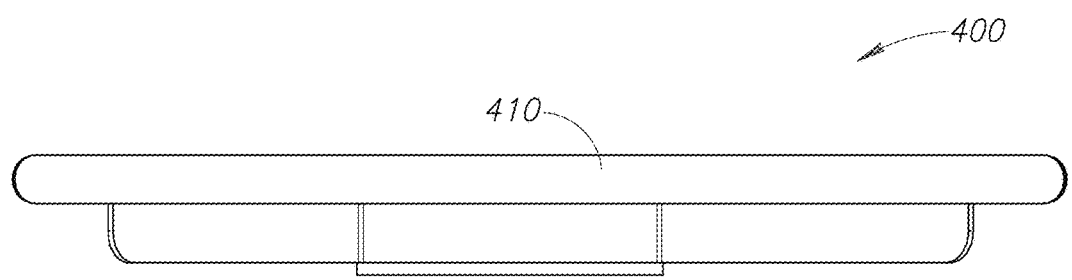
FIG. 7B is a front view of the prior art push handle of FIG. 7A.

In contrast, FIGS. 7A and 7B depict a prior art handle 400 that has a rounded front handle grip 410 with a "flat" shape or grip profile. In other words, as may best be seen in FIG. 7B, the handle grip 410 is substantially horizontal or parallel with the floor. Thus, referring to FIGS. 7A and 7B, the prior art flat handle grip 410 does not follow the natural grip angle (e.g., about 10 angular degrees from horizontal) of the user's hand when the user grabs onto the handle grip 410 at a height (e.g., about 35 inches to about 45 inches from the floor) of the handle 400. Instead, the user must twist his/her wrist to grip the handle grip 410, which can cause undo strain on the user's hand and/or wrist resulting in some discomfort during long-term use.

As mentioned above, referring to FIG. 9, the handle grip 322 is not substantially horizontal (or parallel with the floor). Instead, the handle grip 322 follows the natural grip angle (e.g., about 10 angular degrees from horizontal) of the user's hand when the user grabs onto the handle grip 322 at a height (e.g., about 35 inches to about 45 inches from the floor) of the handle 130.

Referring to FIG. 1, as mentioned above, all or a portion of the handle 130 may extend around the pole 120 (e.g., about 90° or about 180°). For example, referring to FIG. 10, the handle grip 322 may extended circumferentially (in directions identified by arrows 380 and 382) around the pole 120 (see FIG. 1) about 180° to define a "semicircular" shape and increase the size of the handle grip 322 and volume of the tray 340.

By way of a non-limiting example, referring to FIG. 6, the handle body 320 may be constructed as a single piece (e.g., integrally molded with the connector portion 308). The handle body 320 may be constructed from an injection-molded polymer. Alternatively, the handle body 320 may be constructed by die casting (e.g., aluminum). By way of yet of other non-limiting example, the handle body 320 may be constructed by machining or fabricated using another means.

Hook Attachment

Referring to FIG. 1, the hook attachment 140 is configured to be mounted on the pole 120 of the IV stand 100, a pole on a conventional IV stand, a pole of similar mobile equipment, and the like.

Figure 11A:
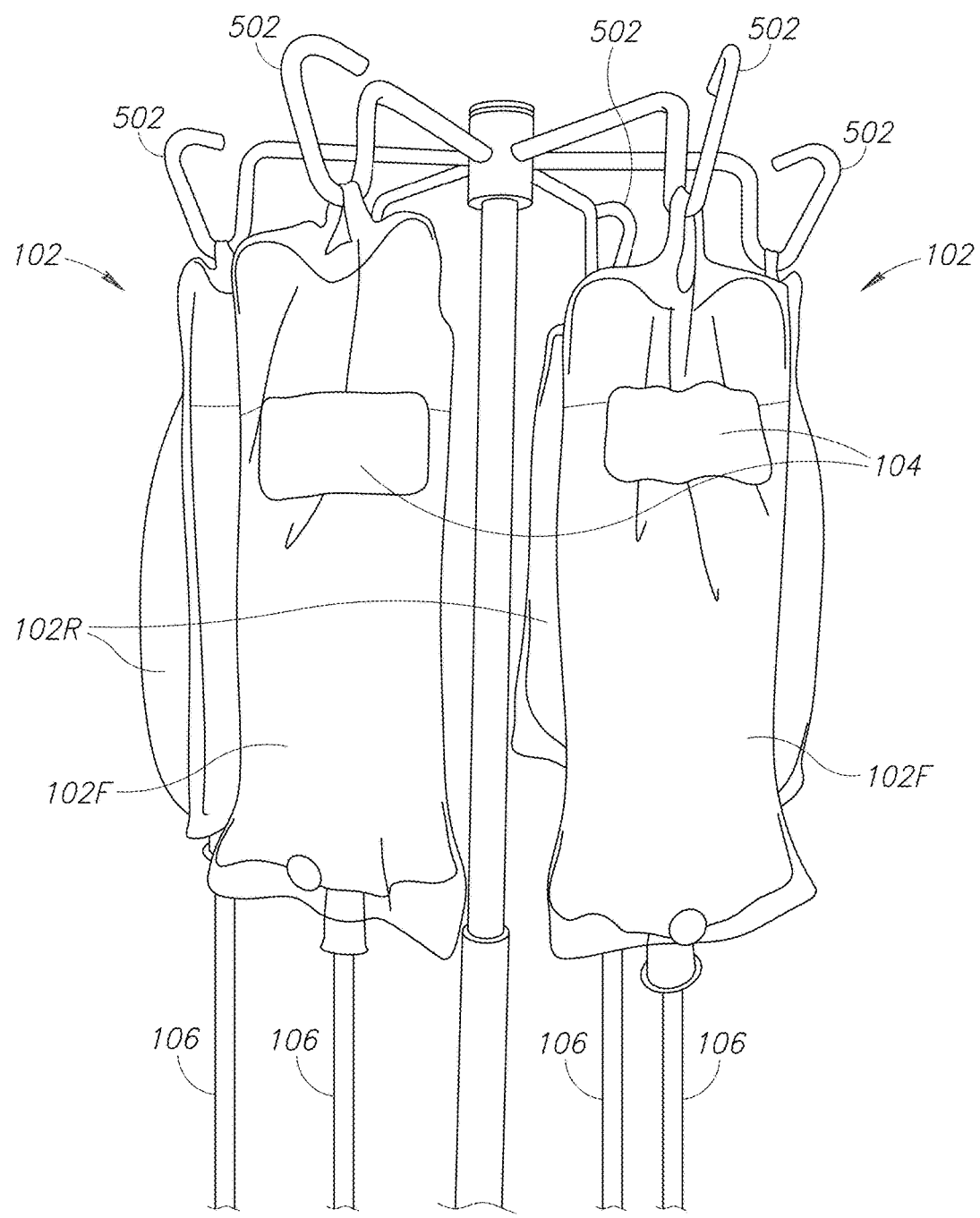
FIG. 11A is a photograph of a prior art IV hook assembly having a plurality of hooks arranged in a circular pattern.
Figure 11B:
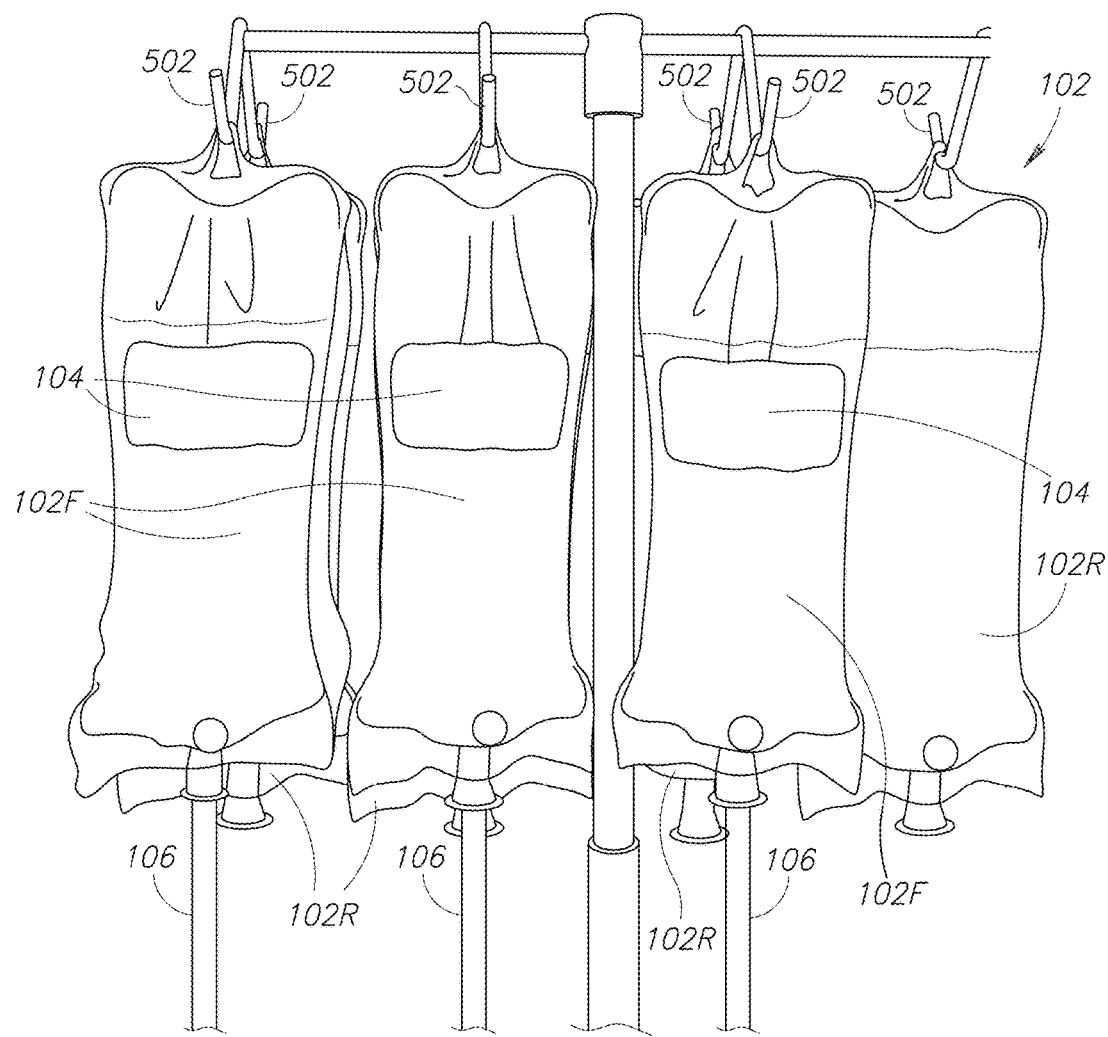
FIG. 11B is a photograph of a prior art IV hook assembly having a plurality of hooks arranged in a longitudinal pattern.

Referring to FIGS. 11A and 11B, prior art IV hook assemblies or attachments include a plurality of hooks 502 typically arranged to allow a plurality of IV bags 102 to be hung in either a circular pattern (FIG. 11A) or longitudinal pattern (FIG. 11B). In both of these arrangements, the IV bags 102 include front bags 102F positioned in front of rear bags 102R. Thus, only the labels 104 on the front bags 102F may be viewed because the labels 104 on the rear bags 102R are hidden or obscured by the front bags 102F. This can pose problems in an operating room ("OR"), an intensive care unit ("ICU"), or other critical area of a hospital where rapid identification of the rear bags 102R is necessary (e.g., to set up infusion pump flows, to monitor patient medication, etc.). Typically, an IV stand is placed against a back wall (e.g., at the head of a bed in the ICU) and several medication lines 106 (e.g., clear tubing) are connected from the bags 102 to the patient. In many cases, due to the entanglement of the medication lines 106, a caregiver cannot turn the IV stand to see the labels 104 on the hidden rear bags 102R. Instead, the caregiver must carefully move or twist the rear bags 102R so the caregiver can read their labels 104. At the same time, the caregiver must be careful not to harm the patient by pulling on the medication lines 106, etc. This takes time and can lead to errors in the identification of one or more of the bags 102. Thus, current hook assemblies or attachments may create potential hazards to patient safety.

Figure 12:
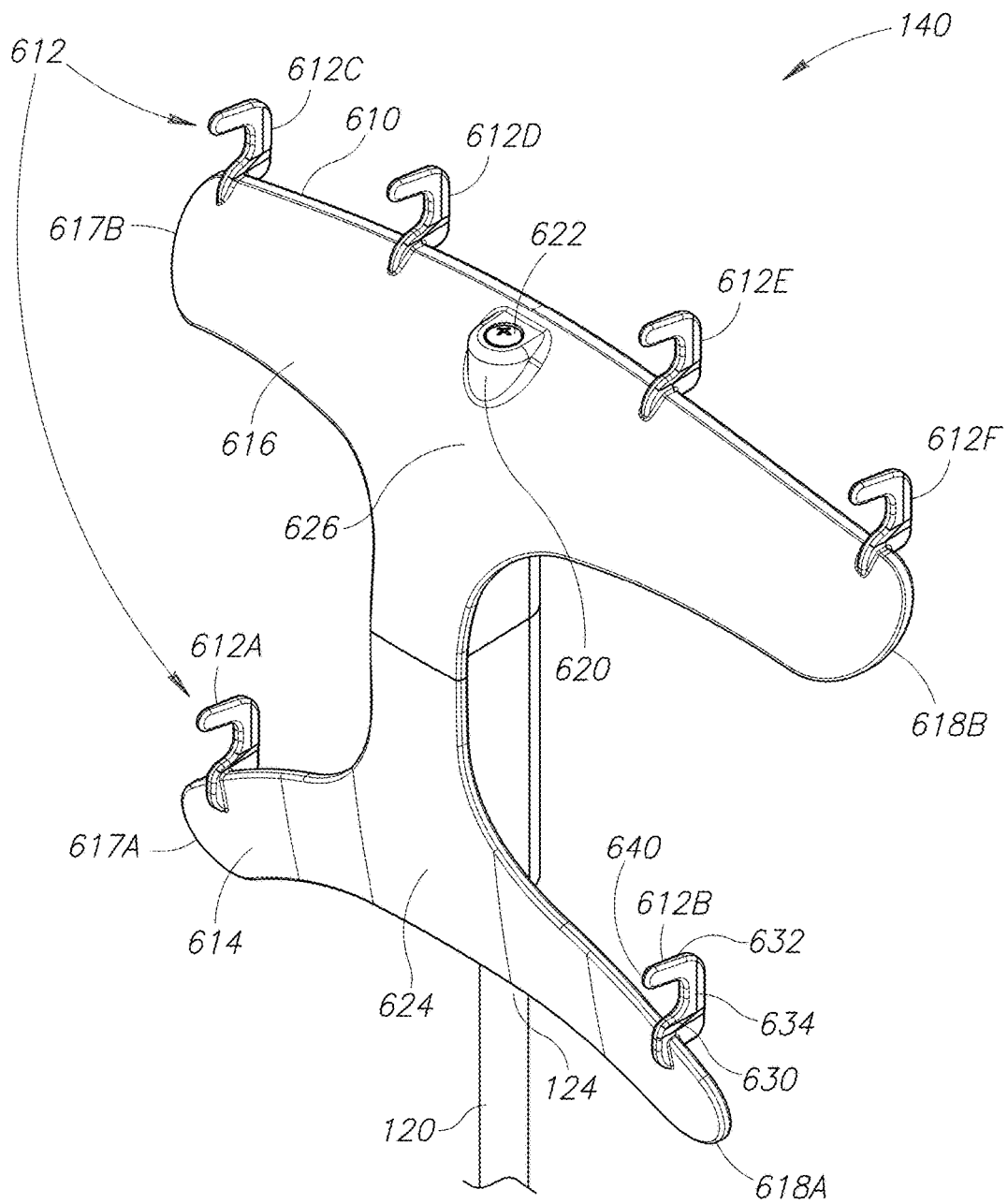
FIG. 12 is a front perspective view of a hook attachment of the IV stand of FIG. 1.

Referring to FIG. 12, the hook attachment 140 has a body portion 610 and a plurality of hooks 612. The body portion 610 has vertically spaced apart first and second longitudinally extending portions 614 and 616. The first portion 614 may have a first free end 617A opposite a second free end 618A. Similarly, the second portion 616 may have a first free end 617B opposite a second free end 618B.

The body portion 610 includes a connector 620 configured to be attached by a fastener 622 (e.g., a screw, a bolt, and the like) to the first end portion 124 of the pole 120 (or a conventional IV pole, a pole of similar mobile equipment, or the like). The connector 620 may be connected to the first and second portions 614 and 616 at near their central portions 624 and 626, respectively.

The hooks 612 are mounted the first and second portions 614 and 616 and are all oriented in the same direction. Thus, the hook attachment 140 does not include both forwardly and rearwardly facing hooks. In the embodiment illustrated, hooks 612A and 612B are positioned on the first portion 614 and hooks 612C-612F are positioned on the second portion 616.

While in the embodiment illustrated in FIGS. 12-14B, the hook attachment 140 includes a total of six hooks (the two hooks 612A and 612B positioned on the first portion 614 and the four hooks 612C-612F positioned on the second portion 616), the hook attachment 140 may be configured with any number of hooks. For example, the hook attachment 140 may include a total of seven hooks, eight hooks, nine hooks, 10 hooks, or more.

Referring to FIGS. 13A and 13B, the opening 103 of one of the bags 102 is configured to receive one of the hooks 612 (see FIG. 12). Thus, each of the hooks 612 (see FIG. 12) is configured to receive and support one of the bags 102 along the bag receiving rear side of the hook attachment 140. The hook attachment 140 is configured to be used facing rearwardly (see FIG. 13A) and/or forwardly (see FIG. 13B). In FIG. 13A, the hook attachment 140 is facing rearwardly with the labels 104 also facing rearwardly. In this configuration, when viewed from the rear as shown in FIG. 13A, lower portions of the bags 102 hanging from the hooks 612C-612F are positioned in front of upper portions of the bags 102 hanging from the hooks 612A and 612B. However, the first and second portions 614 and 616 are spaced apart vertically by a sufficient amount to allow the labels 104 of the bags 102 to be viewed on all of the bags 102. In other words, the hook attachment 140 arranges the bags 102 to provide an unobstructed rear view of the labels 104 of the bags 102.

In FIG. 13B, the hook attachment 140 is facing forwardly with the labels 104 facing forwardly. In this configuration, when viewed from the front as shown in FIG. 13B, lower portions of the bags 102 hanging from the hooks 612C-612F are positioned behind of upper portions of the bags 102 hanging from the hooks 612A and 612B. Nevertheless, the first and second portions 614 and 616 are spaced apart vertically (by the sufficient amount) to allow the labels 104 of the bags 102 to be viewed on all of the bags 102. In other words, the hook attachment 140 arranges the bags 102 to provide an unobstructed front view of the labels 104 of the bags 102.

Thus, as shown in FIGS. 13A and 13B, the hook attachment 140 arranges the bags 102 to provide an unobstructed view of their labels 104 without any need to move the pole 120 and/or twist any of the bags 102.

The hooks 612A and 612B positioned on the first portion 614 are offset longitudinally with respect to the hooks 612C-612F positioned on the second portion 616. In the embodiment illustrated, the hooks 612A and 612B (positioned on the first portion 614) are each spaced apart longitudinally from a nearest one of the hooks 612C-612F positioned on the second portion 616 by a longitudinal distance D3. In the embodiments illustrated, the hooks 612A and 612B (positioned on the first portion 614) are each positioned between an adjacent pair of the hooks 612C-612F (positioned on the second portion 616). For example, in the embodiment illustrated, the hook 612A is positioned between the adjacent pair of hooks 612C and 612D and the hook 612B is positioned between the adjacent pair of hooks 612E and 612F. Thus, the hooks 612A and 612B (positioned on the first portion 614) and the hook(s) 612C-612F (positioned on the second portion 616) may be characterized as being longitudinally offset from one another (e.g., by the longitudinal distance D3). By way of a non-limiting example, the longitudinal distance D3 may be equal to or greater than half a width of one of the labels 104. By way of a non-limiting example, the longitudinal distance D3 may be about 2.25 inches to about 2.75 inches.

The first and second portions 614 and 616 may be symmetric (left to right) about the connector 620. In the embodiment illustrated, the first and second portions 614 and 616 curve downwardly as they extend outwardly from the connector 620. As may be viewed in FIGS. 14A and 14B, the first and second portions 614 and 616 may curve inwardly and/or rearwardly as they extend outwardly from the connector 620. Referring to FIG. 12, the hooks 612C and 612D are positioned on the same side (e.g., the right side) of the connector 620 and the hooks 612E and 612F are positioned on the same side (e.g., the left side) of the connector 620. Thus, on the same side (e.g., the right side) of the connector 620, the hooks 612C and 612D positioned on the second portion 616 are offset from one another along all three dimensions. Similarly, the hooks 612E and 612F, positioned on the second portion 616 on the same side (e.g., the left side) of the connector 620, are offset from one another along all three dimensions.

Figure 14A:
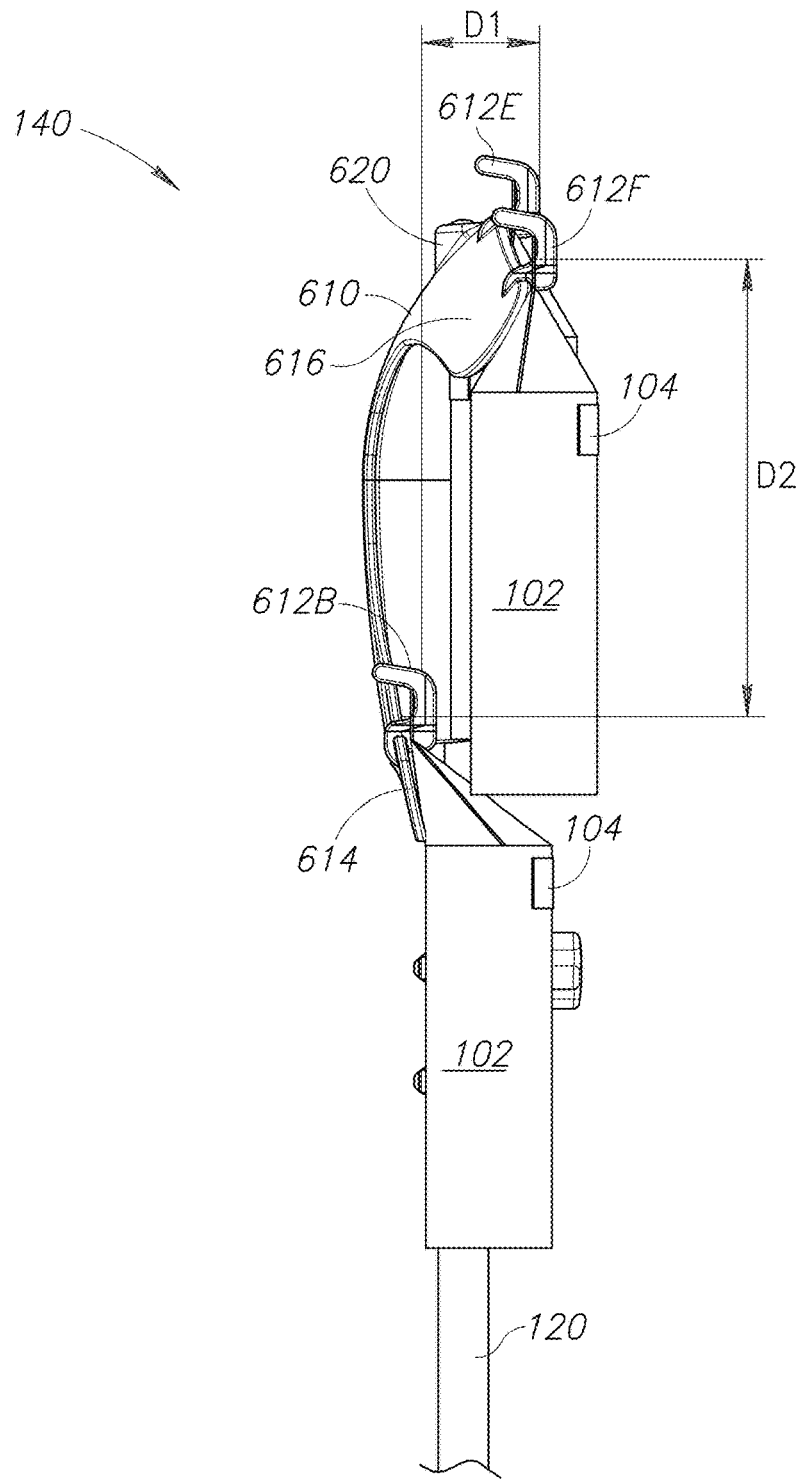
FIG. 14A is a side view of the hook attachment of FIG. 13A illustrated with IV bags hanging therefrom.
Figure 14B:
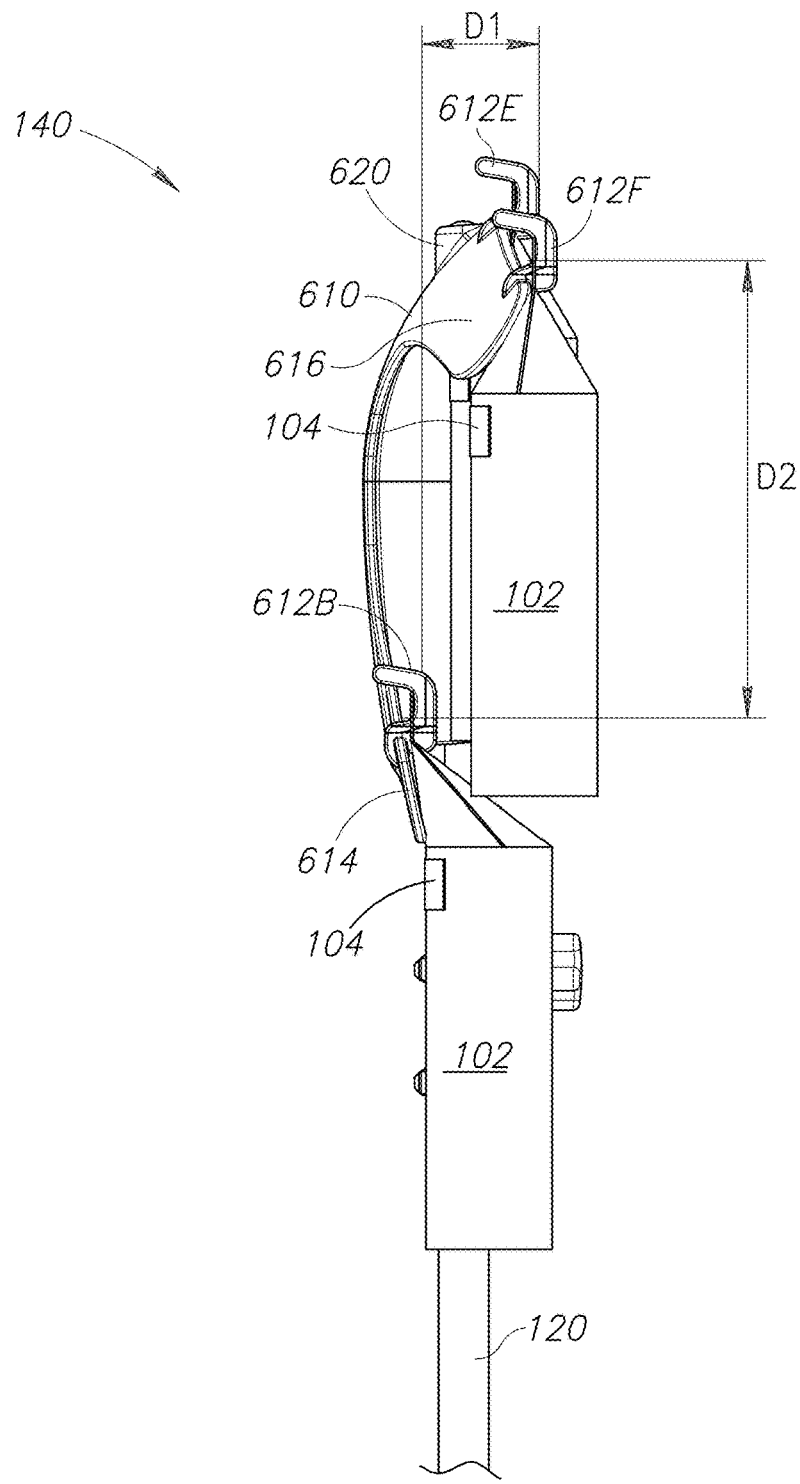
FIG. 14B is a side view of the hook attachment of FIG. 13B illustrated with IV bags hanging therefrom.

Referring to FIGS. 14A and 14B, at least a portion of the body portion 610 positioned between the first and second portions 614 and 616 may curve or bow outwardly away from the pole 120. In the embodiment illustrated, referring to FIG. 12, the front side of the body portion 610 may have a generally convex shape when viewed from the front. As shown in FIGS. 14A and 14B, the body portion 610 may position the second portion 616 further rearward than the first portion 614. Thus, referring to FIG. 13B, the hooks 612C-612F are positioned rearward or behind of the hooks 612A and 612B.

Referring to FIGS. 14A and 14B, in the embodiment illustrated, the hook 612B may be spaced apart laterally (front-to-rear) from the hook 612F by a lateral distance D1. Similarly, referring to FIG. 12, the hook 612A may be spaced apart laterally from the hook 612C by the lateral distance D1 (see FIGS. 14A and 14B). By way of a non-limiting example, the lateral distance D1 may be about 3 inches to about 4.5 inches.

Referring to FIG. 12, in the embodiment illustrated, the hooks 612 are substantially C-shaped and substantially identical to one another. Each of the hooks 612 has a first portion 630 connected to a second portion 632 by a connecting portion 634. The first portion 630 is connected or anchored one of the first and second portions 614 and 616. In the embodiment illustrated, the first portions 630 of the hooks 612A and 612B are mounted on an upper edge of the first portion 614 and the hooks 612A and 612B extend upwardly from the first portion 614. Similarly, the first portions 630 of the hooks 612C-612F are mounted on an upper edge of the second portion 616 and the hooks 612C-612F extend upwardly from the second portion 616. The first portion 630 extends rearwardly away from the body portion 610.

The first portion 630 extends from the body portion 610 to the connecting portion 634. The connecting portion 634 extends upwardly between the first and second portions 630 and 632. The second portion 632 extends forwardly and has a free end portion 640. The second portion 632 extends at an angle from the connecting portion 634 and positions the free end portion 640 above the connecting portion 634.

Referring to FIGS. 13A and 13B, the free end portion 640 is configured to be inserted through the opening 103 of one of the bags 102. Referring to FIG. 12, that bag 102 slides along both the second portion 632 and the connecting portion 634, and rests at or near a junction of the connecting portion 634 and the first portion 630. Thus, the bag 102 is maintained in a desired position between the connecting portion 634 and the bag receiving rear side of the body portion 610. Referring to FIGS. 14A and 14B, in the embodiment illustrated, the junction between the connecting portion 634 (see FIG. 12) and the first portion 630 (see FIG. 12) of the distal most hook 612B (positioned on the first portion 614) is spaced apart vertically from the junction between the connecting portion 634 and the first portion 630 of the distal most hook 612F (positioned on the second portion 616) by a vertical distance D2. Similarly, referring to FIG. 12, the junction between the connecting portion 634 and the first portion 630 of the distal most hook 612A (positioned on the first portion 614) may also be spaced apart vertically from the junction between the connecting portion 634 and the first portion 630 of the distal most hook 612C (positioned on the second portion 616) by the vertical distance D2 (see FIGS. 14A and 14B). The vertical distance D2 may be sufficient to allow the bags 102 to be "piggy-backed." Piggybacking refers to pumping (by gravity head) the contents of an upper bag (e.g., the bag 102 hanging from the hook 612C) and allowing those contents to mix with the output of a lower bag (e.g., the bag 102 hanging from the hook 612A). This mixture is then administered to the patient.

By way of a non-limiting example, the contents of the upper bag may be antibiotics and the contents of the lower bag may be saline solution. Referring to FIGS. 14A and 14B, by way of a non-limiting example, the vertical distance D2 may be at least 9 inches.

In the embodiment illustrated, the first portions 630 have substantially horizontal lower edges that help maintain the bags 102 on the hooks 612. For example, if one of the bags 102 is bumped or pushed upwardly, the first portion 630 of the hook 612 on which the bag is hung blocks upward movement of the bag with respect to the body portion 610. Thus, the first portion 630 significantly reduces a risk that the bag 102 will be disengaged from the hook 612 when the bag 102 (e.g., the bottom of the bag) is inadvertently bumped.

Referring to FIG. 13A, the hook attachment 140 is configured to position the bags 102 such that the label 104 on each of the bags 102 is viewable from the rear without changing the position or orientation of any of the bags 102. Similarly, referring to FIG. 13B, the hook attachment 140 is configured to position the bags 102 such that the label 104 on each of the bags 102 is viewable from the front without changing the position or orientation of any of the bags 102. Thus, when fully loaded with the bags 102, the hook attachment 140 allows the labels 104 of all of the bags 102 to be read from either the front or the rear of the IV stand 100 (or a conventional IV stand) without moving the pole 120 and/or twisting each of the bags 102 after the bags 102 are outfitted with the medication lines 106 (see FIGS. 11A and 11B) and infusion pumps (not shown). This helps reduce label reading errors, improves visibility of the labels 104, facilitates identification of the IV bags 102, and significantly reduces risk to the patient.

By way of a non-limiting example, the hook attachment 140 illustrated in FIGS. 12-14B may be constructed as a single piece. For example, the hook attachment 140 may be constructed from an injection-molded polymer. Alternatively, the hook attachment 140 may be constructed by die casting (e.g., aluminum). By way of yet of other non-limiting example, the hook attachment 140 may be constructed by machining or fabricated using another means.

Figure 15:
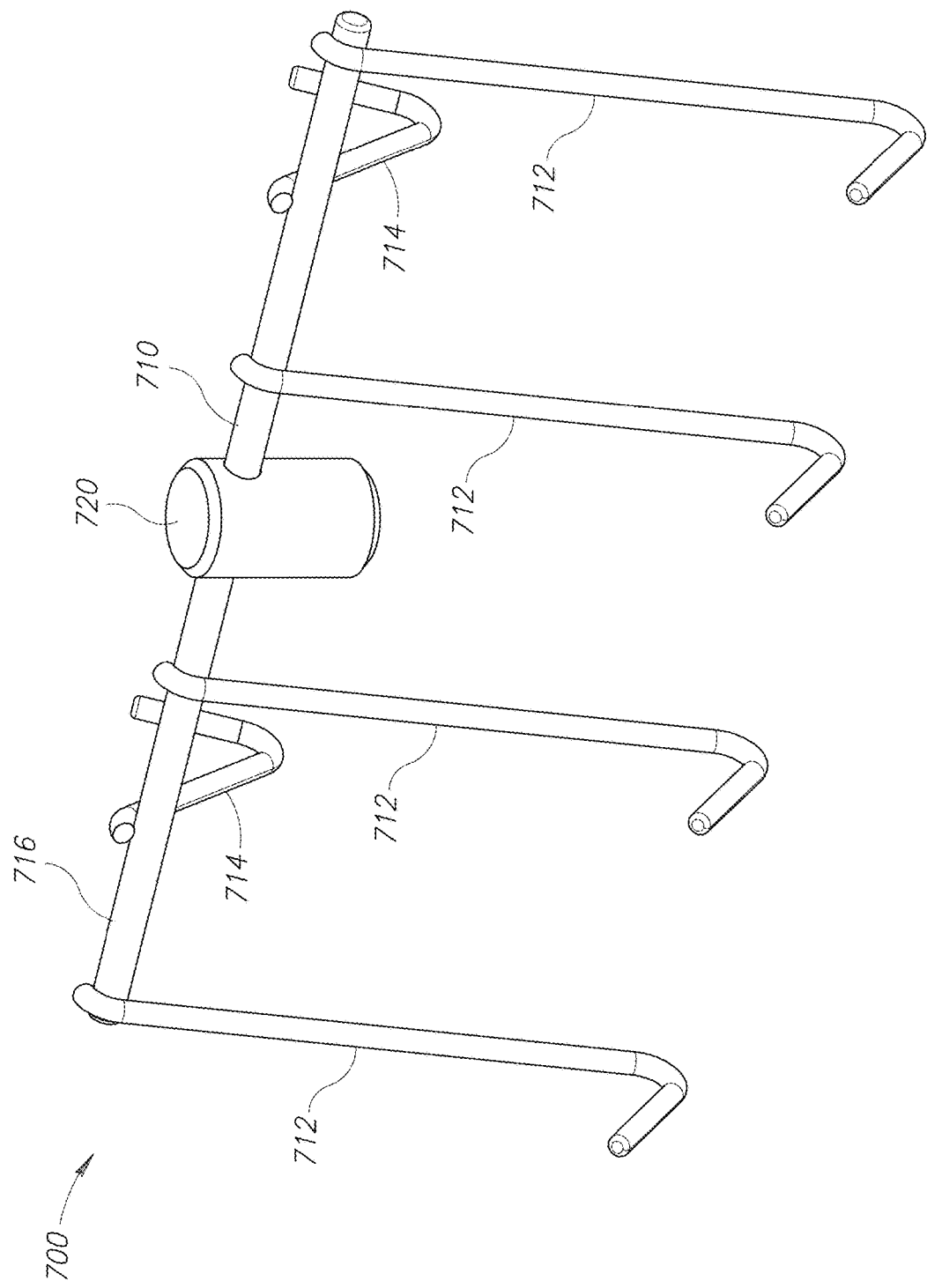
FIG. 15 is a perspective view of an alternate embodiment of a hook attachment.
Figure 16:
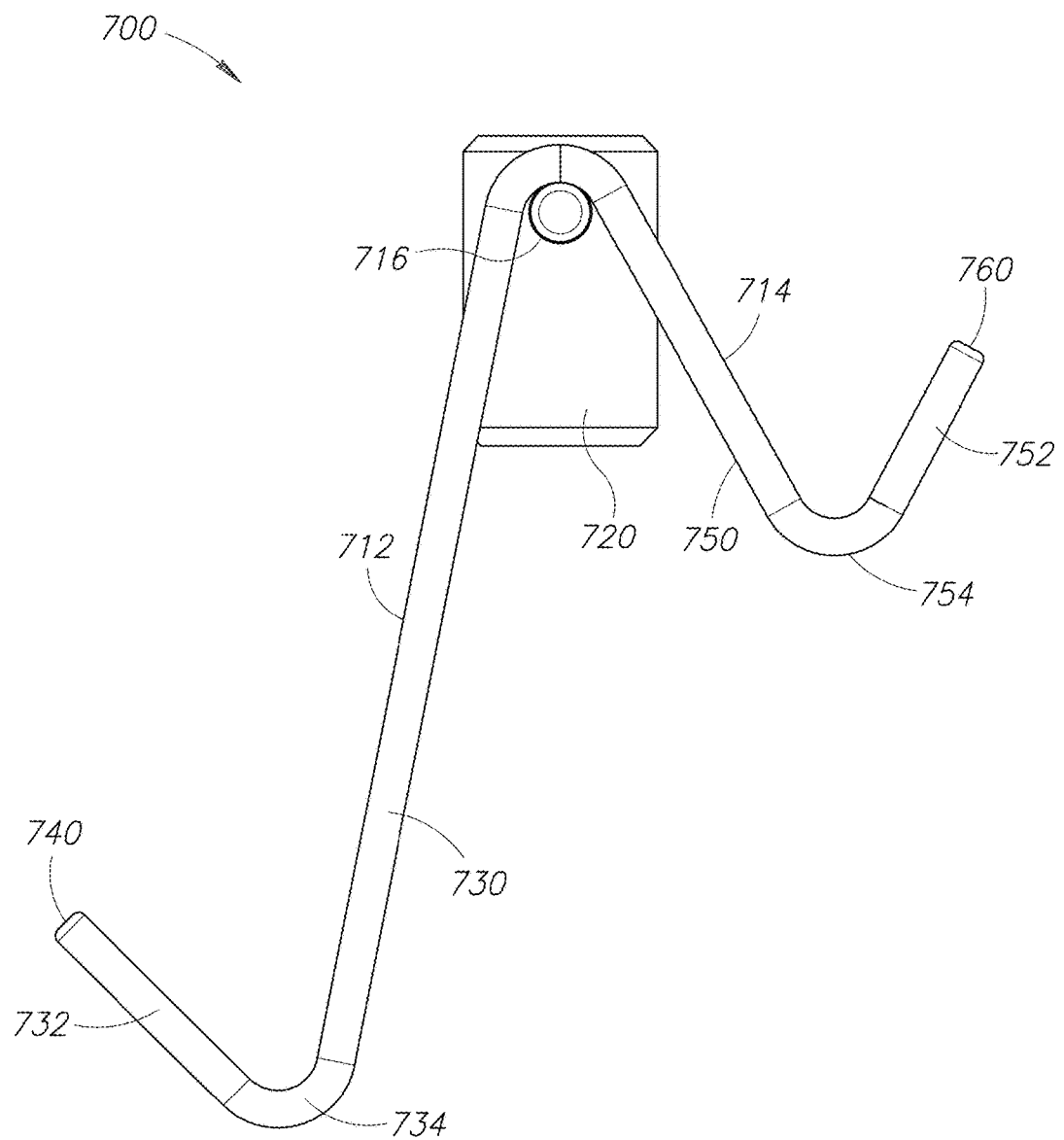
FIG. 16 is a side view of the hook attachment of FIG. 15.

FIGS. 15-18 depict an alternate embodiment of a hook attachment 700 constructed using fabrication. Referring to FIG. 1, like the hook attachment 140, the hook attachment 700 (see FIGS. 15-18) is configured to be mounted on the pole 120 of the IV stand 100, a pole on a conventional IV stand, a pole of similar mobile equipment, and the like. Referring to FIG. 15, the hook attachment 700 has a body portion 710, one or more forward facing or front hooks 712, and one or more rearward facing or rear hooks 714.

The body portion 710 has a longitudinally extending portion 716 from which the front hook(s) 712 and the rear hook(s) 714 extend. Each front hook 712 and each rear hook 714 is positioned at a different longitudinal location along the portion 716. While in the embodiment illustrated, the hook attachment 700 includes a total of six hooks (four front hooks 712 and two rear hooks 714), the hook attachment 700 may be configured with any number of longitudinally spaced apart front and rear hooks. For example, the hook attachment 700 may include a total of seven hooks, eight hooks, nine hooks, 10 hooks, or more.

The body portion 710 has a hub or connector 720 attached near the center of the portion 716. Referring to FIG. 12, the connector 720 (see FIGS. 15-18) may be configured to be attached by a fastener (e.g., a screw, a bolt, and the like) to the first end portion 124 of the pole 120 (a conventional IV pole, a pole of similar mobile equipment, and the like).

Figure 17:
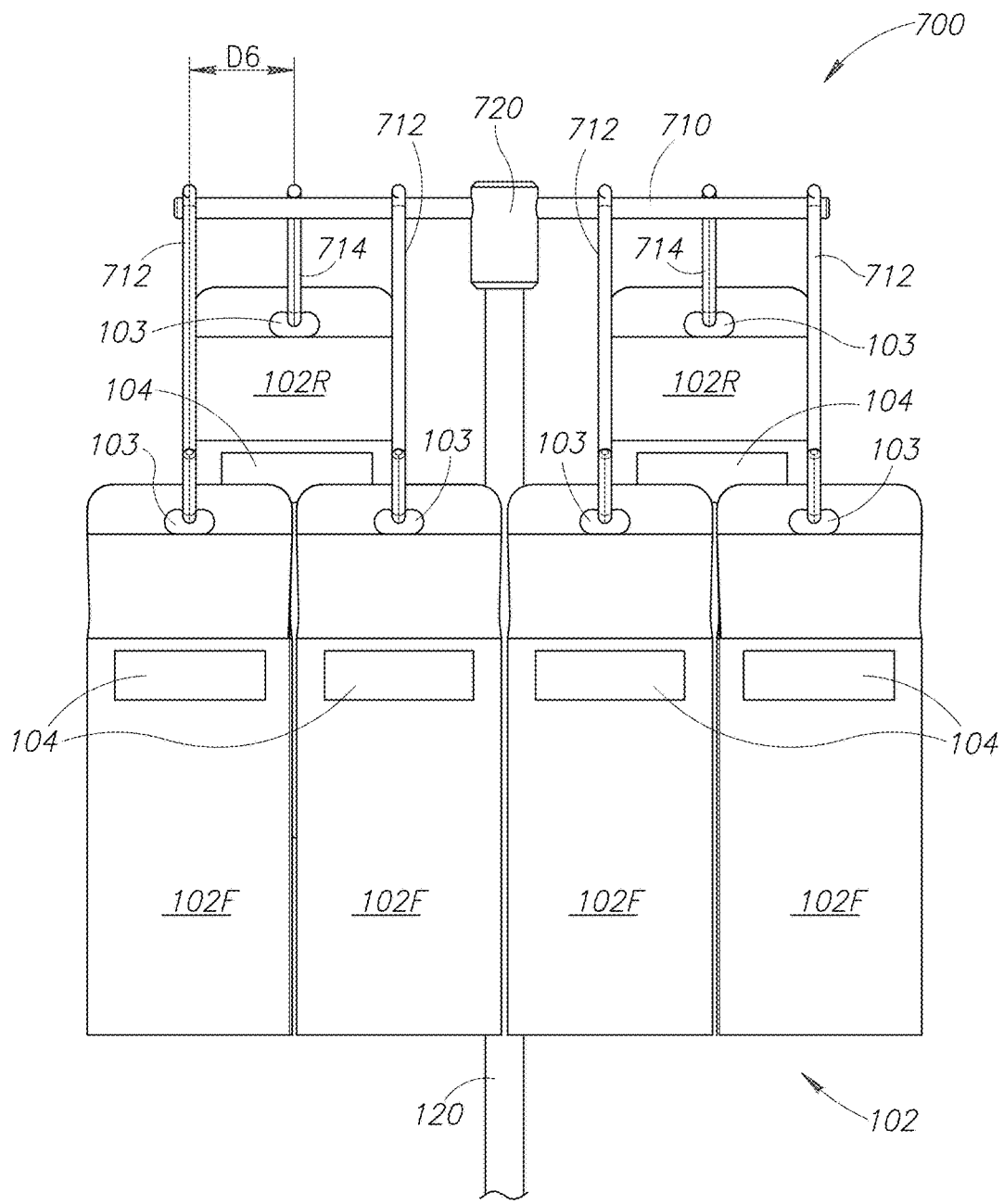
FIG. 17 is a front view of the hook attachment of FIG. 15 illustrated with IV bags hanging therefrom.

Referring to FIG. 17, each front hook 712 is configured to receive and support one of the front bags 102F and each rear hook 714 is configured to receive and support one of the rear bags 102R. The opening 103 of each front bag 102F is configured to receive one of the front hooks 712 and the opening 103 of each rear bag 102R is configured to receive one of the rear hooks 714.

Each rear hook 714 is spaced apart longitudinally from a nearest one of the front hook(s) 712 by a longitudinal distance D6. In the embodiment illustrated, each rear hook 714 is positioned between an adjacent pair of the front hooks 712. Thus, the front hook(s) 712 and the rear hook(s) 714 may be characterized as being longitudinally offset from one another (e.g., by the longitudinal distance D6). When the hook attachment 700 includes multiple front hooks and a rear bag 102R is hung from each of the rear hook(s) 714, the front hooks 712 may be spaced apart longitudinally by a sufficient amount to allow the labels 104 of the rear bag(s) 102R to be viewed between adjacent ones of the front hooks 712. Thus, the longitudinal distance D6 may be equal to or greater than half a width of one of the labels 104. By way of a non-limiting example, the longitudinal distance D6 may be about 2.25 inches to about 2.75 inches.

Figure 18:
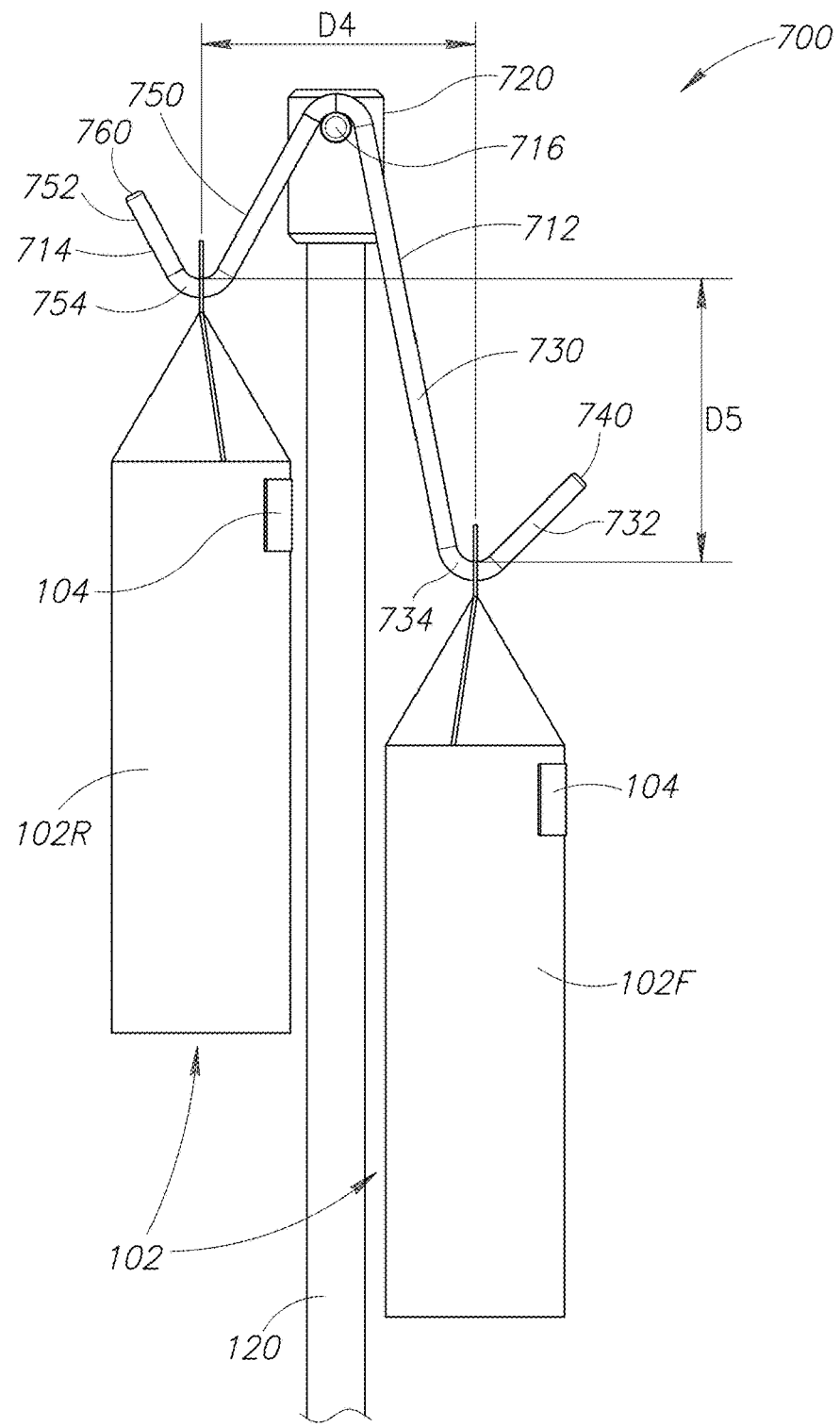
FIG. 18 is a side view of the hook attachment of FIG. 15 illustrated with IV bags hanging therefrom.

Referring to FIG. 18, each front hook 712 has a first portion 730 connected to a second portion 732 by a bent portion 734. The first portion 730 is connected to and extends between the portion 716 and the bent portion 734. The second portion 732 has a free end portion 740. The second portion 732 extends at an angle from the bent portion 734 and positions the free end portion 740 above the bent portion 734. The free end portion 740 is configured to be inserted through the opening 103 (see FIG. 17) of one of the bags 102. One of the front bags 102F slides along the second portion 732 and rests upon the bent portion 734.

Each rear hook 714 has a first portion 750 connected to a second portion 752 by a bent portion 754. The first portion 750 is connected to and extends between the portion 716 and the bent portion 754. The second portion 752 has a free end portion 760. The second portion 752 extends at an angle from the bent portion 754 and positions the free end portion 760 above the bent portion 754. The free end portion 760 is configured to be inserted through the opening 103 (see FIGS. 13A, 13B, 17, and 18) of one of the bags 102. One of the rear bags 102R slides along the second portion 752 and rests upon the bent portion 754.

The first portion 730 of each front hook 712 is longer than the first portion 750 of each rear hook 714 to position the bent portion 734 of each front hook 712 below the bent portion 754 of each rear hook 714. In the embodiment illustrated, the bent portion 734 of each front hook 712 is spaced apart vertically from the bent portion 754 of each rear hook 714 by a vertical distance D5. Thus, the rear bags 102R (which rest upon the bent portion 734 of each rear hook 714) are positioned above the front bags 102F (which rest upon the bent portion 734 of each front hook 712). Therefore, the front hook(s) 712 and the rear hook(s) 714 may be characterized as being vertically offset from one another (e.g., by the vertical distance D5). As shown in FIG. 17, the vertical distance D5 (see FIG. 18) is sufficient to allow the labels 104 of the rear bags 102R to be viewed when the hook attachment 700 includes the front bags 102F. In other words, the hook attachment 700 arranges the front and rear bags 102F and 102R to provide an unobstructed front view of the labels 104 of both the front and rear bags 102F and 102R. Referring to FIG. 18, by way of a non-limiting example, the vertical distance D5 may be about 3 inches to about 4.5 inches.

The second portion 732 of each front hook 712 faces and extends forwardly and the second portion 752 of each rear hook 714 faces and extends rearwardly. Thus, the front and rear hooks 712 and 714 extend in opposite directions from one another. In the embodiment illustrated, a midpoint of the bent portion 734 of each front hook 712 is spaced apart laterally from a midpoint of the bent portion 754 of each rear hook 714 by a lateral distance D4. By way of a non-limiting example, the lateral distance D4 may be about 3 inches to about 4.5 inches. Thus, referring to FIG. 17, the front and rear hooks 712 and 714 are offset from one another longitudinally, laterally, and vertically to position the labels 104 of the rear bags 102R to viewed from the front when the hook attachment 700 includes the front bags 102F.

This arrangement positions the bags 102 such that the label 104 on each rear bag 102R is viewable from the front without changing the position or orientation of the rear bag 102R. Thus, when fully loaded with the bags 102, the hook attachment 700 allows the labels 104 of all of the rear bags 102R to be read from the front of the IV stand 100 (or a conventional IV stand) without moving the pole 120 and/or twisting each of the rear bags 102R after the bags 102 are outfitted with the medication lines 106 (see FIGS. 11A and 11B) and infusion pumps (not shown). This helps reduce label reading errors, improves visibility of the labels 104, facilitates identification of the IV bags 102, and significantly reduces risk to the patient.

Referring to FIG. 15, the hook attachment 700 may be constructed from two or more separate pieces (e.g., each constructed from metal). By way of a non-limiting example, the pieces may include the front hook(s) 712, the rear hook(s) 714, the body portion 710, and the connector 720. The front and rear hooks 712 and 714 may be welded to the body portion 710 and the connector 720.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A base for use by a user having first and second feet, the base comprising:
    a plurality of wheels;
    first, second, third, fourth, and fifth legs supported on the plurality of wheels, the second leg being positioned between the first and third legs, the first leg being positioned between the fourth and second legs, the fifth leg being positioned between the third and the fourth legs, the first and second legs comprising first and second end portions respectively, a keyway being defined between the first and second legs, the first and second legs curving inwardly toward one another and defining an opening into the keyway between the first and second end portions, the fifth leg having a head portion and a connection portion, the head portion being configured to be removably received into a like keyway of a like base, a like opening being defined between like first and second end portions of the like first and second legs, respectively, the base and the like base being interlocked together by the head portion which is too large to pass through the like opening when the head portion is positioned inside the like keyway and the connecting portion of the fifth leg extends outwardly from the like keyway through the like opening;
    a first clearance gap positioned between the second leg and the third leg, the first clearance gap being configured to at least partially receive the user's first foot; and
    a second clearance gap positioned between the fourth leg and the first leg, the second clearance gap being configured to at least partially receive the user's second foot.

2. The base of claim 1, wherein the head portion has a rounded outer shape, and
    the keyway has a rounded inner shape.

3. The base claim 1, the base further comprising:
    a first gap defined between the fifth and fourth legs, the first gap being configured to receive the like first end portion of the like first leg of the like base; and
    a second gap defined between the third and fifth legs, the second gap being configured to receive the like second end portion of the like second leg of the like base.

4. The base claim 1, further comprising:
a bridge portion overhanging a portion of the keyway, the head portion having a free distal end portion configured to be positioned underneath a like bridge portion of the like base when the head portion is positioned inside the like keyway.

5. The base of claim 4, wherein the head portion tapers toward the free distal end portion.

6. The base of claim 1, wherein sufficient space is defined between the head portion and the like keyway to allow the base and the like base to move with respect to one another and remain interlocked together while traversing obstacles.

7. The base of claim 1, wherein the third and fourth legs each extend forwardly, and
the first and second legs each extend rearwardly.

8. The base of claim 1, further comprising:
a center section, the first, second, third, and fourth legs each extending away from the center section other than radially.

9. The base of claim 1, further comprising:
a center section, the first, second, third, and fourth legs each having an upper surface that tapers outwardly and downwardly from the center section.

10. The base of claim 9, wherein the upper surface of each of the first, second, third, and fourth legs is formed along a cone that has an apex at or near the center section.

11. The base of claim 1, further comprising:
a connector configured to receive and retain a pole of an IV stand.

12. A base comprising:
a plurality of legs supported on a plurality of wheels;
a keyway defined between first and second ones of the plurality of legs, the first and second legs having first and second end portions, respectively, that define an opening into the keyway;
a bridge portion overhanging a portion of the keyway; and
a key formed in a third one of the plurality of legs, the key being configured to be removably received inside a like keyway of a like base, and when so received, to interlock the base and the like base together, the like keyway having a like opening defined between like first and second end portions of like first and second legs, respectively, a connecting portion of the third leg being configured to extend outwardly through the like opening but the key being too large to pass through the like opening when the key is received inside the like keyway, the base and the like base being moveable as a unit when interlocked together in both first and second directions, the first direction being opposite the second direction, the unit being movable in the first direction when the base is pushed in the first direction, the unit being movable in the second direction when the base is pulled in the second direction, the key having a free distal end portion, the free distal end portion of the key being positioned underneath a like bridge portion of the like base when the key is removably received inside the like keyway of the like base, the like bridge portion of the like base limiting upward movement of the key relative to the like base.

13. The base of claim 12, wherein the like bridge portion of the like base rests upon and is supported by the key.

14. The base of claim 12, wherein the like bridge portion of the like base straddles the key and is spaced apart therefrom by a pre-determined gap.

15. The base of claim 12, further comprising:
a fourth leg positioned between the first and third legs; and
a first clearance gap positioned between the fourth leg and the first leg, the first clearance gap being configured to at least partially receive a user's foot.

16. The base of claim 15, further comprising:
a fifth leg positioned between the second and third legs; and
a second clearance gap positioned between the fifth leg and the second leg, the second clearance gap being configured to at least partially receive the user's foot.

17. The base of claim 16, the base further comprising:
a first gap defined between the third and fourth legs, the first gap being configured to receive the like first end portion of the like first leg of the like base; and
a second gap defined between the third and fifth legs, the second gap being configured to receive the like second end portion of the like second leg of the like base.

18. The base of claim 12, the base further comprising:
a fourth leg positioned between the first and third legs;
a fifth leg positioned between the second and third legs;
a first gap defined between the third and fourth legs, the first gap being configured to receive the like first end portion of the like first leg of the like base; and
a second gap defined between the third and fifth legs, the second gap being configured to receive the like second end portion of the like second leg of the like base.

19. The base of claim 12, wherein the key tapers toward the free distal end portion.

20. The base of claim 12, wherein sufficient space is defined between the key and the like keyway to allow the base and the like base to move with respect to one another and remain interlocked together while traversing obstacles.

21. The base of claim 12, wherein the first and second legs each curve toward the opening into the keyway.

22. The base of claim 12, the base further comprising:
a fourth leg positioned between the first and third legs; and
a fifth leg positioned between the second and third legs, the fourth and fifth legs each extending forwardly, the first and second legs each extending rearwardly.

23. The base of claim 22, further comprising:
a center section, the first, second, fourth, and fifth legs each extending away from the center section other than radially, the third leg extending away from the center section radially.

24. The base of claim 12, further comprising:
a center section, the first, second, and third legs each having an upper surface that tapers outwardly and downwardly from the center section.

25. The base of claim 24, wherein the upper surface of each of the first, second, and third legs is formed along a cone that has an apex at or near the center section.

26. The base of claim 12, further comprising:
a connector configured to receive and retain a pole of an IV stand.

* * * * *